(12) United States Patent
Kojima et al.

(10) Patent No.: US 8,999,140 B2
(45) Date of Patent: Apr. 7, 2015

(54) GLUCOSE OXIDASE MUTANTS, COMPOSITIONS, DEVICES, KITS AND USES THEREOF

(71) Applicants: Roche Diagnostics Operations, Inc., Indianapolis, IN (US); Ultizyme International, Ltd., Tokyo (JP)

(72) Inventors: Katsuhiro Kojima, Tokyo (JP); Kazushige Mori, Tokyo (JP); Sode Koji, Tokyo (JP)

(73) Assignees: Roche Diagnostics Operations, Inc., Indianapolis, IN (US); Ultizyme International, Ltd., Tokyo (JP)

( * ) Notice: Subject to any disclaimer, the term of this patent is extended or adjusted under 35 U.S.C. 154(b) by 0 days.

(21) Appl. No.: 14/187,753

(22) Filed: Feb. 24, 2014

(65) Prior Publication Data

US 2014/0248645 A1 Sep. 4, 2014

Related U.S. Application Data

(63) Continuation of application No. PCT/EP2012/003572, filed on Aug. 24, 2012.

(30) Foreign Application Priority Data

Aug. 25, 2011 (EP) .................................... 11006939
Mar. 27, 2012 (EP) .................................... 12002193

(51) Int. Cl.
| | | |
|---|---|---|
| *G01F 1/64* | (2006.01) | |
| *C12M 1/00* | (2006.01) | |
| *C12N 15/00* | (2006.01) | |
| *C12N 1/20* | (2006.01) | |
| *C12N 9/04* | (2006.01) | |
| *C12Q 1/00* | (2006.01) | |
| *C12Q 1/26* | (2006.01) | |
| *G01N 27/327* | (2006.01) | |

(52) U.S. Cl.
CPC .............. *C12N 9/0006* (2013.01); *C12Q 1/006* (2013.01); *C12Y 101/03004* (2013.01); *C12Q 1/26* (2013.01); *G01N 27/3271* (2013.01)

(58) Field of Classification Search
USPC ........... 435/190, 6, 252.3, 320.1; 204/403.01; 205/792
See application file for complete search history.

(56) References Cited

U.S. PATENT DOCUMENTS

2004/0053425 A1 3/2004 Link et al.

FOREIGN PATENT DOCUMENTS

EP 1892529 A1 2/2008

OTHER PUBLICATIONS

International Search Report issued May 21, 2013 in Application No. PCT/EP2012/003572, 4 pages.
Bankar, Sandip B. et al., "Glucose oxidase—An overview," Biotechnology Advances, Jul. 2009, pp. 489-501, vol. 27, No. 4.

*Primary Examiner* — Maryam Monshipouri
(74) *Attorney, Agent, or Firm* — Roche Diagnostics Operations, Inc.

(57) ABSTRACT

Compositions, devices, kits and methods are disclosed for assaying glucose with a glucose oxidase mutant that has been modified at an amino acid residue involved in the active site. The glucose oxidase mutant has reduced oxidase activity while substantially maintaining its dehydrogenase activity.

17 Claims, 1 Drawing Sheet

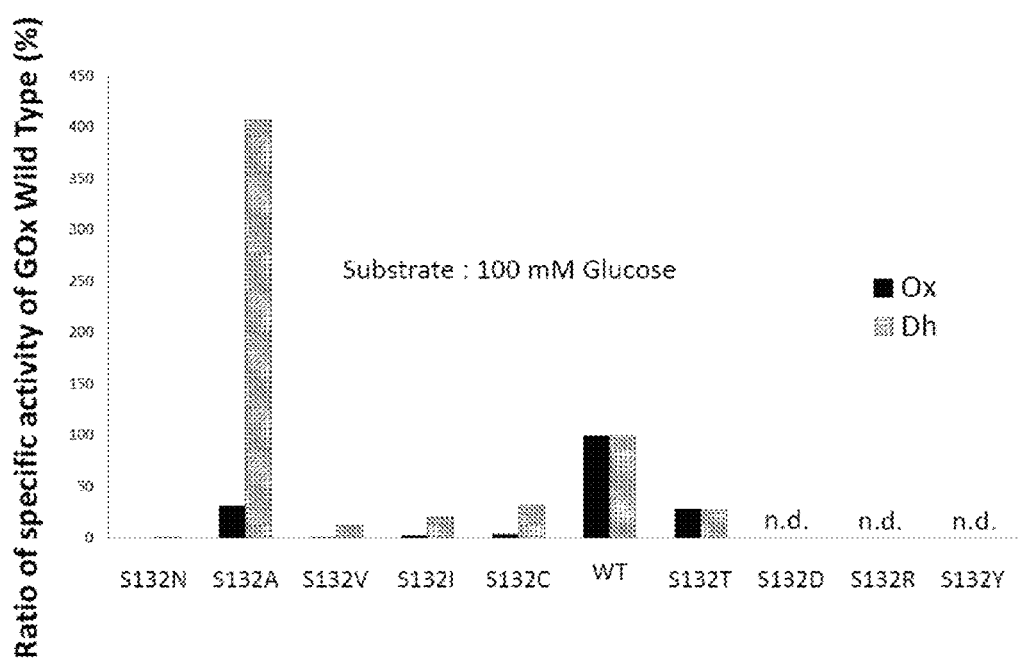

US 8,999,140 B2

GLUCOSE OXIDASE MUTANTS, COMPOSITIONS, DEVICES, KITS AND USES THEREOF

CROSS-REFERENCE TO RELATED APPLICATIONS

This patent application is a continuation of Int'l Patent Application No. PCT/EP2012/003572 (filed 24 Aug. 2012), which claims the benefit of EP Patent Application Nos. 11006939.0 (filed 25 Aug. 2011) and 12002193.6 (filed 27 Mar. 2012). Each patent application is incorporated herein by reference as if set forth in its entirety.

REFERENCE TO SEQUENCE LISTING SUBMITTED ELECTRONICALLY

An official copy of a Sequence Listing is submitted electronically via EFS-Web as an ASCII-formatted Sequence Listing with a file named "27499SequenceListing.txt," created on 22 Jan. 2014, and having a size of 112 KB. The Sequence Listing is filed concurrently with the Specification, is a part thereof and is incorporated herein by reference as if set forth in its entirety.

TECHNICAL FIELD

This disclosure relates generally to chemistry, medicine and molecular biology, and more particularly, it relates to a glucose oxidase mutant having a reduced oxidase activity that can be used in a biosensor test strip, enzyme electrode, sensor and/or kit for measuring glucose.

BACKGROUND

The concentration of glucose in blood is important in clinical tests for diagnosing diabetes mellitus and in controlling blood-sugar of individuals having diabetes mellitus. Blood glucose may be measured using an enzyme having specificity to glucose such as, for example, glucose oxidase (GOx).

GOx has been isolated from various kinds of strains and it has been suggested that glucose may be analyzed using such enzymes. GOx is a flavin adenine dinucleotide (FAD)-dependent enzyme that catalyzes a reaction where glucose is oxidized to generate gluconolactone, thereby generating the reduced form of FAD, $FADH_2$. $FADH_2$, in turn, transmits electrons to an electron acceptor and is converted back to its oxidized form. In the presence of oxygen, $FADH_2$ preferentially transmits electrons to oxygen molecules rather than to artificial electron acceptors (also referred to as mediators or electron mediators). Thus, when glucose is assayed by GOx with mediators, the assay results will be greatly affected by the dissolved oxygen level in the reaction system. Such a disadvantage will be particularly noted in clinical tests of blood samples by a point-of-care testing device utilizing an artificial electron acceptor. Therefore, enzymes used for enzyme biosensor test strips employing artificial electron mediators desirably have low activity toward oxygen.

For the foregoing reason, there is a need for an enzyme, in particular, a GOx having an activity that is less affected by the dissolved oxygen level.

BRIEF SUMMARY

An inventive concept described herein is an enzyme, in particular, a GOx having an activity that is less affected by a dissolved oxygen level. This concept is achieved by reducing the oxidase activity of an enzyme that in its wild-type form predominantly shows an oxidase activity and also by preferably at the same time increasing the enzyme's dehydrogenase activity. As will be described in more detail below, this has been achieved by modifying the wild-type enzyme.

The disclosure describes various GOx mutants, and it was surprisingly found that a certain type of mutants exhibits reduced oxidase activity while substantially retaining dehydrogenase activity, in particular dye-mediated dehydrogenase activity.

In an aspect, a GOx mutant is provided. In some instances, the GOx mutant can be modified at one or more positions such as:

(a). a position corresponding to position 53 of the amino acid sequence set forth in SEQ ID NO: 1 by substituting the amino acid residue Thr with another amino acid residue;

(b). a position corresponding to position 116 of the amino acid sequence set forth in SEQ ID NO: 1 by substituting the amino acid residue Ile with another amino acid residue;

(c). a position corresponding to position 132 of the amino acid sequence set forth in SEQ ID NO: 1 by substituting the amino acid residue Ser or Thr with another amino acid residue;

(d). a position corresponding to position 134 of the amino acid sequence set forth in SEQ ID NO: 1 by substituting the amino acid residue Thr with another amino acid residue;

(e). a position corresponding to position 237 of the amino acid sequence set forth in SEQ ID NO: 1 by substituting the amino acid residue Ile or Phe with another amino acid residue;

(f). a position corresponding to position 371 of the amino acid sequence set forth in SEQ ID NO: 1 by substituting the amino acid residue Val or Ala with another amino acid residue;

(g). a position corresponding to position 373 of the amino acid sequence set forth in SEQ ID NO: 1 by substituting the amino acid residue Phe with another amino acid residue;

(h). a position corresponding to position 434 of the amino acid sequence set forth in SEQ ID NO: 1 by substituting the amino acid residue Glu with another amino acid residue;

(i). a position corresponding to position 436 of the amino acid sequence set forth in SEQ ID NO: 1 by substituting the amino acid residue Phe with another amino acid residue;

(j). a position corresponding to position 448 of the amino acid sequence set forth in SEQ ID NO: 1 by substituting the amino acid residue Trp with another amino acid residue; and (k). a position corresponding to position 537 of the amino acid sequence set forth in SEQ ID NO: 1 by substituting the amino acid residue Trp with another amino acid residue.

In other instances, the GOx mutant can be modified at one or more positions such as:

(a). a position corresponding to position 53 of the amino acid sequence set forth in SEQ ID NO: 1 by substituting the amino acid residue Thr with Ser;

(b). a position corresponding to position 116 of the amino acid sequence set forth in SEQ ID NO: 1 by substituting the amino acid residue Ile with Val;

(c). a position corresponding to position 132 of the amino acid sequence set forth in SEQ ID NO: 1 by substituting the amino acid residue Ser with Ala, Thr, Val, Cys or Ile, or by substituting the amino acid residue Thr with Ala, Ser, Val, Trp or Cys;

(d). a position corresponding to position 134 of the amino acid sequence set forth in SEQ ID NO: 1 by substituting the amino acid residue Thr with Ala, Ile or Met;

(e). a position corresponding to position 237 of the amino acid sequence set forth in SEQ ID NO: 1 by substituting the amino acid residue Ile with Val, or by substituting the amino acid residue Phe with Ile, Ala, Val, Met, Ser, Asp, Leu, Thr, Asn, Arg or Cys;

(f). a position corresponding to position 371 of the amino acid sequence set forth in SEQ ID NO: 1 by substituting the amino acid residue Val with Thr, Ala, or by substituting the amino acid residue Ala with Val;

(g). a position corresponding to position 373 of the amino acid sequence set forth in SEQ ID NO: 1 by substituting the amino acid residue Phe with Leu, Tyr, Ala, Met, Asn or Trp;

(h). a position corresponding to position 434 of the amino acid sequence set forth in SEQ ID NO: 1 by substituting the amino acid residue Glu with Gln;

(i). a position corresponding to position 436 of the amino acid sequence set forth in SEQ ID NO: 1 by substituting the amino acid residue Phe with Trp, Ala, Leu, Tyr, Met, Glu or Ile;

(j). a position corresponding to position 448 of the amino acid sequence set forth in SEQ ID NO: 1 by substituting the amino acid residue Trp with Ala, Ile, Ser, Val, Met, Thr, Cys, Gly, Leu, Asn, Asp, Lys, Phe, Gln or Tyr; and (k). a position corresponding to position 537 of the amino acid sequence set forth in SEQ ID NO: 1 by substituting the amino acid residue Trp with Ala.

Regardless of the substitution, the GOx mutant has a reduced oxidase activity when compared to a wild-type GOx. In other instances, the GOx mutant also has an increased dehydrogenase activity when compared to the wild-type GOx. Specifically, the GOx mutant can have an oxidase activity of about 30% or less than that of the wild-type GOx and optionally can have an increased dehydrogenase activity when compared to the wild-type GOx. In some instances, the GOx mutant has a dehydrogenase activity of about 50% or more when compared to the wild-type GOx.

In another aspect, an isolated polynucleotide is provided that encodes a GOx mutant as described herein.

In another aspect, a vector is provided that includes a polynucleotide encoding a GOx mutant as described herein.

In another aspect, a host cell is provided that is transformed with a vector as described herein.

In another aspect, a device is provided for assaying glucose in a sample, where the device includes a GOx mutant as described herein and optionally an electron mediator. In some instances, an enzyme electrode is provided, where the enzyme electrode includes a GOx mutant as described herein that is immobilized on the electrode. In other instances, an enzyme sensor is provided for assaying glucose, where the enzyme sensor includes an enzyme electrode as described herein as a working electrode.

In another aspect, a kit is provided for assaying glucose in a sample, where the kit includes a GOx mutant as described herein and optionally an electron mediator.

In view of the foregoing, a method is provided for assaying glucose in a sample. The method can include contacting the sample with a GOx mutant as described herein and then measuring an amount of glucose oxidized by the GOx mutant. In some instances, the GOx mutant is incorporated into a device such as a biosensor test strip, enzyme electrode or sensor as described herein.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF DRAWINGS

The advantages, effects, features and objects other than those set forth above will become more readily apparent when consideration is given to the detailed description below. Such detailed description makes reference to the following drawings, wherein:

FIG. 1 shows ratios of the oxidase (Ox) and dehydrogenase (Dh) activities at a glucose substrate concentration of 100 mM of various GOx mutants compared to wild-type GOx. "n.d." in FIG. 1 and in the tables means "not detected."

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments above and the claims below. Reference should therefore be made to the embodiments above and claims below for interpreting the scope of the inventive concept. As such, it should be noted that the embodiments described herein may have advantages, effects, features and objects useful in solving other problems.

DESCRIPTION OF PREFERRED EMBODIMENTS

The compositions, devices, kits and methods now will be described more fully hereinafter, in which some, but not all embodiments of the inventive concept are shown. Indeed, the compositions, devices, kits and methods may be embodied in many different forms and should not be construed as limited to the embodiments set forth herein; rather, these embodiments are provided so that this disclosure will satisfy applicable legal requirements.

Likewise, many modifications and other embodiments of the compositions, devices, kits and methods described herein will come to mind to one of skill in the art to which the disclosure pertains having the benefit of the teachings presented in the foregoing description. Therefore, it is to be understood that the compositions, devices, kits and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the inventive concept pertains. Although any methods and materials similar to or equivalent to those described herein can be used in the practice or testing of the compositions, devices, kits and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Exemplary compositions, devices, kits and methods are provided for measuring glucose and are based upon a GOx mutant less affected by a dissolved oxygen level. This concept can be achieved at the very least by reducing the oxidase activity of the GOx mutant when compared to a wild-type GOx. In addition, the GOx mutant can be modified to increase its dehydrogenase activity when compared to the wild-type GOx. This concept is in contrast to current compositions, devices, kits and methods that largely rely on wild-type GOx.

Such compositions, devices, kits and methods incorporating a GOx mutant as described herein are useful in a variety of applications. For example, the GOx mutant may be used for measuring glucose, which is clinically useful in diagnosing and controlling diabetic conditions.

The work described herein is the first to show that the disadvantages noted above can be solved with a GOx mutant having at least a reduced oxidase activity and optionally an increased dehydrogenase activity. The present inventive concept therefore provides compositions, devices, kits and methods for measuring glucose.

Compositions

Glucose Oxidase Mutants: One composition encompassing the inventive concept includes an isolated, GOx mutant that exhibits decreased oxidase (or Ox) activity when compared to a wild-type GOx while substantially retaining dehydrogenase (or Dh) activity. In some instances, the GOx mutant further exhibits an increased Dh activity when compared to the wild-type GOx.

As used herein, "isolated," with respect to a polypeptide (and also a polynucleotide), means a molecule (e.g., polypeptide, protein or polynucleotide) isolated from its natural environment or prepared using synthetic methods such as those known to one of skill in the art. Complete purification is not required in either case. The molecules described herein can be isolated and purified from normally associated material in conventional ways, such that in the purified preparation the molecule is the predominant species in the preparation. At the very least, the degree of purification is such that extraneous material in the preparation does not interfere with use of the molecule in the manner disclosed herein. The molecule is at least about 85% pure; alternatively, at least about 90% pure, alternatively, at least about 95% pure; and alternatively, at least about 99% pure.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "mutant," when used in connection with a polypeptide or protein such as an enzyme, means a variant containing a substitution in one or more of the amino acid residues on the polypeptide or protein at the indicated position(s). Mutant also is used for a polynucleotide encoding such a mutant polypeptide or protein.

As used herein, "a position corresponding to" means the position of an amino acid residue in a query amino acid sequence that is aligned with the amino acid residue in a reference amino acid sequence using software such as AlignX of Vector NTI with default parameters (available from Invitrogen; see, Lu & Moriyama (2004) Brief Bioinform. 5:378-88). Thus, "amino acid (AA) residue at a position corresponding to the position Y of the amino acid sequence set forth in SEQ ID NO: X" means the AA residue in a query amino acid sequence that is aligned with AA Y of SEQ ID NO: X when the query amino acid sequence is aligned with SEQ ID NO: X using AlignX of Vector NTI with default parameters. It should be noted that the AA Y of SEQ ID NO: X itself is also encompassed by this term.

As used herein, "oxidase activity" or "Ox activity" means an enzymatic activity of the GOx mutant to catalyze oxidation of glucose to generate gluconolactone by utilizing oxygen as an electron acceptor. The oxidase activity may be assayed by measuring the amount of generated $H_2O_2$ by any method known in the art such as, for example, by reagents for $H_2O_2$ detection such as 4AA/TODB/POD (4-aminoantipyrine/N, N-bis(4-sulfobutyl)-3-methylaniline disodium salt/horseradish peroxidase) or by a platinum (Pt) electrode. In the context of the relative or quantitative activity, the oxidase activity is specifically defined to be the mole amount of the substrate (glucose) oxidized per unit time measured by the amount of generated $H_2O_2$ at about 25° C. in 10 mM PPB, pH 7.0, 1.5 mM TODB, 2 U/ml horseradish peroxidase (POD), and 1.5 mM 4-aminoantipyrine (4AA). The formation of quinoneimine dye may be measured spectrophotometrically at 546 nm.

As used herein, "dehydrogenase activity" or "Dh activity" means an enzymatic activity of the GOx mutant to catalyze oxidation of glucose to generate gluconolactone by utilizing an electron mediator other than oxygen as an electron acceptor. The dehydrogenase activity may be assayed by measuring the amount of electron transferred to the mediator using, for example, mPMS/DCIP (1-methoxy-5-methylphenazinium methylsulfate/2,6-dichloroindophenol), cPES (trifluoro-acetate-1-(3-carboxy-propoxy)-5-ethyl-phenanzinium, NA BM31__1144 (N,N-bis-(hydroxyethyl)-3-methoxy-nitrosoaniline hydrochloride, NA BM31__1008 (N,N-bis-hydroxyethyl-4-nitrosoaniline) and N—N-4-dimethyl-nitrosoaniline. In the context of the relative or quantitative activity, the dehydrogenase activity is specifically defined to be the mole amount of the substrate (e.g., glucose) oxidized per unit time measured by the amount of electron transferred to the mediator at about 25° C. in 10 mM PPB (pH 7.0), 0.6 mM DCIP, and 6 mM methoxy PMS (mPMS).

The GOx mutant therefore has a reduced oxidase activity when compared to the wild-type GOx, while substantially retaining the dehydrogenase activity. The GOx mutant can have an oxidase activity of about 50% or less when compared to the wild-type GOx. Alternatively, the GOx mutant has an oxidase activity of about 40% or less, about 30% or less, about 20% or less, or about 15% or less when compared to the wild-type GOx.

In addition, the GOx mutant can have a dehydrogenase activity of about 50% or more when compared to a wild-type GOx. Alternatively, the GOx mutant has a dehydrogenase activity of about 60% or more, about 70% or more, about 80% or more, about 90% or more, about 100% or more, or more than 100% or more when compared to the wild-type GOx.

In the wild-type GOx, the oxidase activity is about 3 to 4 times higher than the dehydrogenase activity. When dissolved oxygen is present in an assay system, electrons generated by oxidizing the substrate can be transferred to oxygen. Thus, the enzyme activity measured in the presence of an electron mediator will be greatly affected by the dissolved oxygen concentration. In contrast, the GOx mutant as described herein has a ratio of dehydrogenase/oxidase activity of about 2.0 or more, about 4.0 or more, about 6.0 or more, about 8.0 or more, or about 10 or more. Since the dehydrogenase activity exceeds the oxidase activity, the enzyme activity of the GOx mutant will be less affected by the dissolved oxygen concentration, which is advantageous in utilizing the GOx mutant in a clinical diagnosis with a blood sample.

It should be understood that the numbering of the amino acid sequence for GOx herein begins at the initial Met and that the claimed GOx mutant may or may not have the signal peptide. Examples of amino acid sequences for the GOx mutant include, but are not limited to, SEQ ID NOs: 1-21 modified at least at one of a position corresponding to position 53, 116, 132, 134, 237, 371, 373, 434, 436, 448 or 537 of SEQ ID NO: 1.

GOx Mutant-Encoding Polynucleotides: Another composition encompassing the inventive concept includes an isolated polynucleotide that encodes a GOx mutant as described herein. An isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

The nucleotide sequence of polynucleotides coding for GOx may be readily obtained from public databases such as, for example, GenBank®, European Nucleotide Archive, DNA Databank of Japan, and Int'l Nucleotide Sequence Database Collaboration.

The polynucleotide encoding the wild-type GOx may be cloned from the genome of respective organisms using PCR or other known techniques. The mutations may be introduced by techniques such as site-directed mutagenesis, PCR mutagenesis or any other known techniques. The amino acid residue to be mutated may be identified using any software for sequence alignment available in the art. Alternatively, polynucleotides coding for the GOx mutant may be prepared by PCR using a series of chemically synthesized oligonucleotides, or fully synthesized. Examples of nucleotide sequences for the GOx mutant can include, but are not limited to, those encoding an amino acid sequence as set forth in any one of SEQ ID NOs: 1-21 modified at least at one of a position corresponding to position 53, 116, 132, 134, 237, 371, 373, 434, 436, 448 or 537 of SEQ ID NO: 1.

Vectors and Host Cells: Other compositions encompassing the inventive concept include a vector having the GOx mutant-encoding polynucleotide or a host cell expressing the vector. The GOx mutant may be prepared by inserting a mutant polynucleotide into an appropriate expression vector and introducing the vector into an appropriate host cell, such as, for example, *Escherichia coli*. The transformant is cultured and the GOx mutant expressed in the transformant may be collected from the cells or culture medium by any known technique.

The recombinant GOx mutant thus obtained may be purified by any of the known purification techniques including, but not limited to, ion exchange column chromatography, affinity chromatography, liquid chromatography, filtration, ultrafiltration, salt precipitation, solvent precipitation, immunoprecipitation, gel electrophoresis, isoelectric electrophoresis and dialysis.

Thus, the inventive concept encompasses isolated or purified polypeptides, proteins and polynucleotides for a GOx mutant, a vector comprising the polynucleotide encoding the GOx mutant, a host cell transformed with such a vector, and a method for preparing the GOx mutant by culturing the transformant, collecting and purifying the GOx mutant from the culture.

Devices

In addition to the above compositions, the inventive concept encompasses various devices for assaying glucose in a sample, where the device includes a GOx mutant as described herein and an electron mediator.

Biosensor Test Strips: One device encompassing the inventive concept includes biosensor test strips having at least the GOx mutant as described herein as a reagent. The assay device may have a similar structure as any conventional, commercially available electrochemical (e.g., amperometric) biosensor test strip for monitoring the blood glucose level. One example of such a device has two electrodes (i.e., a working electrode and a reference or counter electrode) positioned on an insulating substrate, a reagent port and a sample receiver. The reagent port contains the GOx mutant and an electron mediator.

When a sample such as blood sample is added to the sample receiver, glucose contained in the sample will react with GOx and the electron mediator to generate a current, which is indicative of the amount of glucose in the sample. Examples of electrochemical biosensors for determining enzyme substrates are known in, for example, Int'l Patent Application Publication No. WO 2004/113900 and U.S. Pat. No. 5,997,817.

As an alternative to electrochemical sensors, optical detection technologies might be used. Typically, such optical devices are based on color changes that occur in a reagent system comprising an enzyme, an electron mediator and an indicator. The color changes can be quantified using fluorescence, absorption or remission measurements. Examples of optical devices suited for determining enzyme substrate concentration are known in, for example, U.S. Pat. Nos. 7,008,799; 6,036,919 and 5,334,508.

Enzyme Electrodes: Another device encompassing the inventive concept includes an enzyme electrode having at least the GOx mutant immobilized on the electrode.

Enzyme Sensors: Another device encompassing the inventive concept includes an enzyme sensor for assaying glucose having an enzyme electrode as described herein as a working electrode. The concentration of glucose in a sample may be determined by measuring the amount of electrons generated by the enzyme reaction. Various sensor systems are known in the art and include, but are not limited to, carbon (C) electrode, metal electrode and Pt electrode.

Here, the GOx mutant can be immobilized on electrodes. Examples of means for immobilizing molecules such as the GOx mutant include, but are not limited to, cross-linking, encapsulating into a macromolecular matrix, coating with a dialysis membrane, optical cross-linking polymer, electro-conductive polymer, oxidation-reduction polymer, and any combination thereof.

When the measurement is conducted in an amperometric system using a C electrode, gold (Au) electrode or Pt electrode provided with an immobilized enzyme is used as a working electrode, together with a counter electrode (such as a Pt electrode) and a reference electrode (such as Ag/AgCl electrode). The electrodes can be inserted into a buffer containing a mediator and kept at predetermined temperature.

A predetermined voltage can be applied to the working electrode, and then a sample is added and an increased value in electric current is measured. Examples of the mediators for use in the assay include, but are not limited to, potassium ferricyanide, ferrocene, osmium derivative, ruthenium derivative, phenazine methosulfate, etc. It is generally also possible to use so-called two-electrode systems with one working electrode and one counter or pseudo-reference electrode.

Further, glucose may be assayed using an immobilized electron mediator in an amperometric system using a C electrode, Au electrode or Pt electrode. The enzyme, such as a GOx mutant, can be immobilized on the electrode together with an electron mediator such as potassium ferricyanide, ferrocene, osmium derivative, or phenazine methosulfate in a macromolecular matrix by means of adsorption or covalent bond to prepare a working electrode.

The working electrode can be inserted into buffer together with a counter electrode (such as a Pt electrode) and a reference electrode (such as a Ag/AgCl electrode), and kept at a predetermined temperature. As indicated above, a predetermined voltage can be applied to the working electrode, and then the sample is added and increased value in electric current is measured.

Thus, the inventive concept encompasses biosensor test strips, electrodes and sensors including at least the GOx mutant as described herein.

Kits

In addition to the above compositions and devices, the inventive concept encompasses kits for assaying glucose in a sample, where the kits include at least a GOx mutant as described herein and optionally an electron mediator.

Additionally, the kits can include a buffer necessary for the measurement, an appropriate electron mediator and, if necessary, further enzymes such as peroxidase, a standard solution of glucose for preparing a calibration curve and an instruction for use. The GOx mutant may be provided in various forms such as, for example, a freeze-dried reagent or a solution in an appropriate storage solution.

Any or all of the kit reagents can be provided within containers that protect them from the external environment, such as in sealed containers. Positive and/or negative controls can be included in the kits to validate the activity and correct usage of reagents employed in accordance with the inventive concept. Controls can include samples known to be either positive or negative for the presence of a predetermined concentration of glucose. The design and use of controls is standard and well within the routine capabilities of one of skill in the art.

Methods

In addition to the compositions, devices and kits, the inventive concept encompasses methods of assaying glucose in a sample.

The method can include at least a step of contacting the sample with the GOx mutant and a step of measuring the amount of the glucose oxidized by the GOx mutant as described above and further below.

EXAMPLES

The inventive concept will be more fully understood upon considering the following non-limiting examples, which are offered for purposes of illustration, not limitation.

Example 1

Plasmids Expressing GOx of *Penicillium amagasakiens* pET22 gox WT was used as a plasmid expressing GOx of *P. amagasakiens* (GenBank® Accession No. AADO1493). This plasmid has a DNA fragment containing the region of the GOx structural gene derived from *P. amagasakiens* except for the signal sequence, which is inserted in the NheI/EcoRI cloning site of a vector pET22. The GOx gene in this plasmid is controlled by a T7 promoter. The pET22 gox WT contains an ampicillin resistance gene.

Example 2

Mutagenesis of the GOx Structural Gene Derived from *P. amagasakiens*

(1). Mutagenesis of residues 132 and 373.

The *P. amagasakiens*-derived GOx structural gene contained in the pET22 gox WT obtained in Example 1 was mutagenized such that Ser at residue 132 and Phe at residue 373 in GOx encoded by this gene were substituted by other amino acid residues.

Specifically, the codon (TCC) for Ser at residue 132 and the codon (TTC) for Phe at residue 373 in the GOx structural gene contained in the plasmid pET22 gox WT described in Example 1 were substituted by other amino acid codons using a commercially available site-directed mutagenesis kit (Stratagene Corp., QuikChange II Site-Directed Mutagenesis Kit).

The sequences of forward and reverse primers used in the amino acid residue substitution are shown in the tables below, The number represents a position in the amino acid sequence containing the signal sequence of GOx; the alphabet described before the number represents an amino acid residue before amino acid substitution; and the alphabet described after the number represents an amino acid residue after amino acid substitution. For example, S132A represents the substitution of Ser at residue 132 to Ala.

In PCR reaction, a reaction solution of the composition shown below was subjected to reaction at 95° C. for 30 seconds and then 15 repetitive cycles each involving 95° C. for 30 seconds, 55° C. for 1 minute and 68° C. for 8 minutes, followed by 68° C. for 30 minutes and then kept at 4° C.

Composition of Reaction Solution:

| | |
|---|---|
| Template DNA (5 ng/μL) | 2 μL |
| 10x reaction buffer | 5 μL |
| Forward primer (100 ng/μL) | 1.25 μL |
| Reverse primer (100 ng/μL) | 1.25 μL |
| dNTP | 1 μL |
| Distilled water | 38.5 μL |
| DNA polymerase | 1 μL |
| Total | 50 μL |

After the PCR reaction, 0.5 μL of DpnI was added to the reaction solution and incubated at 37° C. for 1 hour to degrade the template plasmid.

*E. coli* DH5a (supE44, ΔlacU169 (φ80lacZΔM15), hsdR17, recA1, endA1, gyrA96, thi-1, relA1) competent cells were transformed with the obtained reaction solution. From colonies grown on an LB agar medium (1% Bacto tryptone, 0.5% yeast extracts, 1% sodium chloride, 1.5% agar) containing kanamycin (50 μg/mL), plasmid DNA was prepared and sequenced to confirm that the mutation of interest was introduced in the GOx structural gene.

The plasmid confirmed to have the introduced mutation was digested with restriction enzymes NheI and HindIII to excise the mutagenized GOx structural gene, which was in turn inserted to a pET28a vector. DH5a was transformed with this plasmid, and a plasmid was extracted from the obtained colonies to obtain a GOx mutant expression plasmid.

TABLE 1

Primer for S132.

| Amino acid substitution | Primer name | Sequence | SEQ ID NO |
|---|---|---|---|
| S132A | S132AFw | 5' CTTGATAAACGGTGACGCGTGGACTCGCCC 3' | 22 |
| S132A | S132ARv | 5' GGGCGAGTCCACGCGTCACCGTTTATCAAG 3' | 23 |

TABLE 2

Primer for F373.

| Amino acid substitution | Primer name | Sequence | SEQ ID NO |
|---|---|---|---|
| F373A | F373AFw | 5' CAGGCCGTCTTCGCGGCCAATTTCACTGAG 3' | 24 |
| F373A | F373ARv | 5' CTCAGTGAAATTGGCCGCGAAGACGGCCTG 3' | 25 |
| F373L | F373LFw | 5' GTCAGGCCGTCTTCCTGGCCAATTTCACTGAG 3' | 26 |
| F373L | F373LRv | 5' CTCAGTGAAATTGGCCAGGAAGACGGCCTGAC 3' | 27 |
| F373P | F373PFw | 5' CAGGCCGTCTTCCCGGCCAATTTCACTGAG 3' | 28 |
| F373P | F373PRv | 5' CTCAGTGAAATTGGCCGGGAAGACGGCCTG 3' | 29 |
| F373W | F373WFw | 5' CAGGCCGTCTTCTGGGCCAATTTCACTGAG 3' | 30 |
| F373W | F373WRv | 5' CTCAGTGAAATTGGCCCAGAAGACGGCCTG 3' | 31 |
| F373Y | F373YFw | 5' CAGGCCGTCTTCTACGCCAATTTCAC 3' | 32 |
| F373Y | F373YRv | 5' GTGAAATTGGCGTAGAAGACGGCCTG 3' | 33 |

Example 3

Analysis of Enzymatic Activity of Mutant GOx

Methods:

Mutant GOx was produced using the mutant GOx expression plasmid obtained in Example 2, and studied for its enzymatic activity.

(1). Culture.

*E. coli* strain BL21 (DE3) was transformed with the wild-type GOx expression plasmid prepared in Example 1 or the mutant GOx expression plasmid prepared in Example 2. These transformants were separately shake-cultured at 37° C. for 12 hours in 3 mL of an LB medium (containing 100 μg/mL ampicillin) using an L-shaped tube. 1 mL each of these culture solutions was inoculated to a 500-mL Erlenmeyer flask with a baffle containing 100 mL of an LB medium (containing 100 μg/mL ampicillin) and gyratory-cultured at 37° C. At the point in time when $OD_{600}$ reached around 0.6, IPTG (isopropyl-β-D-thiogalactopyranoside) was added thereto at a final concentration of 0.5 mM, followed by culture at 20° C. for 24 hours.

(2). Preparation of Inclusion Body Fraction.

From the culture solution thus cultured, bacterial cells were collected and washed. Then, the obtained wet bacterial cells were suspended in a 20 mM potassium phosphate buffer (pH 6.8) and sonicated. Then, the homogenate was centrifuged at 17400×g at 4° C. for 20 minutes, and the precipitate was used as an insoluble fraction.

The obtained insoluble fraction was washed with a washing solution (1) (potassium phosphate buffer pH 6.8+100 mM NaCl+1 mM EDTA+1% Triton X-100) and centrifuged at 10000×g at 4° C. for 10 minutes. The precipitate was washed with a washing solution (2) (potassium phosphate buffer pH 6.8+100 mM NaCl+1 mM EDTA) and centrifuged at 10000×g at 4° C. for 10 minutes. The precipitate was further washed with a washing solution (3) (2 M urea+20 mM potassium phosphate buffer pH 6.8) and centrifuged at 10000×g at 4° C. for 10 minutes. The inclusion body was collected as a precipitate, where GOx forms the greatest part of this inclusion body.

(3). Refolding of Inclusion Body.

The inclusion body thus prepared was suspended in a solubilizing buffer (8 M urea+30 mM dithiothreitol (DTT)+20 mM potassium phosphate buffer pH 6.8), and this suspension was used as a solubilized inclusion body fraction. The solubilized inclusion body was diluted with a solubilizing buffer to a protein concentration of 0.1 mg/mL and dialyzed against a 100-fold volume or more of a refolding buffer (1 mM glutathione (reduced form)+1 mM glutathione (oxidized form)+0.05 mM flavin adenine dinucleotide+10% (w/v) glycerol (vol/vol)+20 mM potassium phosphate buffer pH 6.8) for 24 hours. Then, the resulting dialyzed solution was further dialyzed against 20 mM potassium phosphate buffer (pH 6.8) for 12 hours and centrifuged at 17400×g at 4° C. for 3 minutes for removing protein aggregates. The supernatant was used as a GOx sample to determine GOx and glucose dehydrogenase (GDH) activities at 25° C. for each of wild-type GOx and mutant GOx.

(4). Determining GOx Activity.

GOx activity was determined by quantifying a change in absorbance at 546 nm over time derived from a dye generated using peroxidase, a Trinder reagent (TODB), and 4-aminoantipyrine from hydrogen peroxide generated through reaction with the substrate. The reaction was performed under conditions shown below.

The reaction was initiated by adding the substrate to a reaction solution (10 mM potassium phosphate buffer pH 7.0+1.5 mM 4-aminoantipyrine+1.5 mM TODB+2 U/ml peroxidase; all the concentrations are final concentrations) containing the enzyme solution, and change in absorbance at 546 nm was determined. Various concentrations of glucose were used as the substrate. The amount of an enzyme that forms 1 µmol $H_2O_2$ for 1 minute is defined as 1 U. 38 mM-1 cm$^{-1}$ was used as the molar absorption coefficient of TODB at pH 7.0. The formula for calculating an activity value from change in absorbance is shown below.

$$U/ml = \Delta ABS_{546}/min \times 2/38 \times 10$$

$$U/mg = U/ml/protein\ mg/ml$$

(5). Determining GDh Activity.

GDh activity was determined by quantifying a change in absorbance at 600 nm over time derived from the fading of DCIP reduced through reaction with the substrate. The reaction was performed under conditions shown below.

The reaction was initiated by adding the substrate to a reaction solution (10 mM potassium phosphate buffer pH 7.0+0.6 mM PMS+0.06 mM DCIP; all the concentrations are final concentrations) containing the enzyme solution, and change in absorbance at 600 nm was determined. Those used in the GOx activity determination were used as the substrate. The amount of an enzyme that reduces 1 µmol DCIP is defined as 1 U. The activity value was calculated according to the formula shown below. 16.3 mM-1 cm$^{-1}$ was used as the molar absorption coefficient of DCIP at pH 7.0.

$$U/ml = \Delta ABS_{600}/min \times 1/16.3 \times 5$$

$$U/mg = U/ml/protein\ mg/ml$$

Results:

The results of activity determination of the wild-type GOx and the mutant GOx are shown in Tables 3 and 4 (different runs). Moreover, a graph showing the ratios of the oxidase and dehydrogenase activities of various mutants at a glucose substrate concentration of 10 mM to the wild-type activities is shown in FIG. 1. The S132 and F373 mutants had reduced oxidase activity and improved dehydrogenase activity, compared with the wild-type. Among them, the S132A mutant had dehydrogenase activity improved to 4 times or more the wild-type and oxidase activity reduced to approximately 40% of the wide-type.

TABLE 3

| | GOx (U/mg) Substrate (mM) | | GDh (U/mg) Substrate (mM) | | GDh/GOx (%) Substrate (mM) | |
|---|---|---|---|---|---|---|
| | 10 | 100 | 10 | 100 | 10 | 100 |
| WT | 9.05 (100%) | 15.0 (100%) | 2.25 (100%) | 3.83 (100%) | 24.8 | 25.6 |
| F373A | 1.38 (15.2%) | 1.53 (10.3%) | 2.68 (119%) | 3.38 (88.2%) | 194 | 220 |
| F373L | 7.62 (84.2%) | 10.0 (67.1%) | 4.38 (195%) | 6.27 (164%) | 57.5 | 62.4 |
| F373W | 2.91 (32.2%) | — | 0.496 (22.0%) | — | 17.0 | — |
| F373Y | 6.94 (76.7%) | 10.2 (68.0%) | 1.35 (60.0%) | 2.03 (53.0%) | 19.4 | 20.0 |

TABLE 4

| | GOx (U/mg) Substrate (mM) | | GDh (U/mg) Substrate (mM) | | GDh/GOx (%) Substrate (mM) | |
|---|---|---|---|---|---|---|
| | 10 | 100 | 10 | 100 | 10 | 100 |
| WT | 31.3 (100%) | 47.4 (100%) | 8.13 (100%) | 13.1 (100%) | 26 | 27.7 |
| S132A | 10.8 (34.5%) | 14.9 (31.4%) | 24.3 (299%) | 53.5 (408%) | 225 | 360 |
| S132C | 0.592 (1.89%) | 1.86 (3.92%) | 0.779 (9.58%) | 4.21 (32.1%) | 132 | 226 |
| S132I | 0.171 (0.55%) | 1.16 (2.46%) | 0.319 (3.92%) | 2.74 (20.9%) | 186 | 236 |
| S132N | 0.0098 (0.03%) | 0.0514 (0.11%) | 0.0169 (0.21%) | 0.185 (1.41%) | 173 | 360 |
| S132R | n.d. | n.d. | n.d. | n.d. | — | — |
| S132D | n.d. | n.d. | n.d. | n.d. | — | — |
| S132T | 6.94 (29.1%) | 11.2 (28.9%) | 1.84 (27.7%) | 3.02 (26.9%) | 26.5 | 27.1 |
| S132V | 0.0858 (0.36%) | 0.531 (1.38%) | 0.298 (4.49%) | 1.37 (12.2%) | 347 | 259 |
| S132Y | n.d. | n.d. | n.d. | n.d. | — | — |
| S132E | n.d. | n.d. | n.d. | n.d. | — | — |
| S132H | n.d. | n.d. | n.d. | n.d. | — | — |
| S132M | n.d. | 0.0265 (0.06%) | n.d. | 0.101 (0.84%) | — | 380 |
| S132Q | n.d. | 0.0399 (0.08%) | n.d. | 0.17 (1.42%) | — | 426 |
| S132A/ F373A | 0.358 (3.96%) | 0.434 (2.9%) | 3.55 (158%) | 8.07 (211%) | 991 | 1.86 × 10$^3$ |
| S132A/ F373L | 2.65 (29.3%) | 3.2 (21.4%) | 8.75 (389%) | 19.7 (515%) | 330 | 616 |

Example 4

Preparation and Analysis of Enzymatic Activity of Wild-Type and Mutant GOx-Derived from *Apergillus niger*

Wild type and mutant GOx from *A. niger* (SwissProt P13006) were prepared in the same manner as described in Examples 1 and 2. The Thr residue at 132 and Phe reside at 373 of *A. niger* (SwissProt P13006) correspond to Ser residue at 132 and Phe residue at 373 of *P. amagasakiens* (GenBank® AAD01493), respectively.

Mutant GOx from *A. niger* was prepared and its enzymatic activity was analyzed in the same manner as described in Example 3. The results from wild type and mutant GOxs are summarized in Table 5 below.

TABLE 5

| | GOx (U/mg) Substrate (mM) | | GDh (U/mg) Substrate (mM) | | GDh/GOx (%) Substrate (mM) | |
|---|---|---|---|---|---|---|
| | 50 | 200 | 50 | 200 | 50 | 200 |
| WT | 3.43 (100%) | 5.01 (100%) | 1.37 (100%) | 2 (100%) | 40 (100%) | 40 (100%) |
| T132A | 2.46 (71.7%) | 3.82 (76.2%) | 4.04 (295%) | 10.1 (502%) | 164 (411%) | 263 (658%) |
| T132S | 6.64 (193%) | 10.2 (204%) | 4.43 (322%) | 7.13 (356%) | 66.7 (167%) | 69.7 (174%) |
| F373Y | 2.05 (59.8%) | 3.14 (62.8%) | 1.16 (84.1%) | 2.08 (104%) | 56.3 (141%) | 66.2 (165%) |

Tables 6 and 7 show alignment of the amino acid sequences that are annotated to be GOxs. The entire sequences of these GOx mutants are set forth in SEQ ID NOs: 1-21. Alignment was created using the AlignX application of Vector NTI suite 6.0. One of skill in the art will appreciate that other alignment software programs such as Blast will provide the same or substantially the same alignment.

It is evident from Table 6 that Ser132 of SEQ ID NO:1 is conserved among the amino acid sequences listed in Table 6. Accordingly, one of skill in the art can easily identify the Ser or Thr residue corresponding to the Ser132 of SEQ ID NO:1 within the conserved region using any of commercially available software programs for sequence alignment, and understand that a GOx mutant is easily prepared by introducing modification on that Ser or Thr residue.

TABLE 6

| Origin* | Position of mutation | | | SEQ ID NO** |
|---|---|---|---|---|
| gb\|AAD01493 | S132 | 122 | LGGSTLINGD<u>S</u>WTRPDKVQID 142 | 1 |
| gb\|ABM63225 | S132 | 122 | LGGSTLINGD<u>S</u>WTRPDKVQID 142 | 2 |
| sp\|Q92452 | S132 | 122 | LGGSTLINGD<u>S</u>WTRPDKVQID 142 | 3 |
| ref\|XP_002482295 | S163 | 153 | LGGSTLINGD<u>S</u>WTRPDKIQID 173 | 4 |
| emb\|CAE47418 | S132 | 122 | LGGSTLINGD<u>S</u>WTRPDKVQID 142 | 5 |
| ref\|XP_002563451 | S132 | 122 | LGGSTLINGD<u>S</u>WTRPDKVQID 142 | 6 |
| ref\|XP_001217613 | S156 | 146 | LGGSTLINGD<u>S</u>WTRPDKVQID 166 | 7 |
| ref\|XP_001215424 | S130 | 120 | LGGSTLINGD<u>S</u>WTRPDKVQID 140 | 8 |
| ref\|XP_001727544 | S133 | 123 | LGGSTLINGG<u>S</u>WTRPDKVQID 143 | 9 |
| ref\|XP_002375824 | S133 | 123 | LGGSTLINGG<u>S</u>WTRPDKVQID 143 | 10 |
| ref\|XP_001216461 | S133 | 123 | LGGSTLVNGG<u>S</u>WTSPDKVQLD 143 | 11 |
| gb\|ADP03053 | T110 | 100 | LGGSTLVNGG<u>T</u>WTRPHKAQVD 120 | 12 |
| gb\|ACR56326 | T132 | 122 | LGGSTLVNGG<u>T</u>WTRPHKAQVD 142 | 13 |
| sp\|P13006 | T132 | 122 | LGGSTLVNGG<u>T</u>WTRPHKAQVD 142 | 14 |
| gb\|ABG54443 | T108 | 98 | LGGSTLVNGG<u>T</u>WTRPHKAQVD 118 | 15 |
| gb\|AAV68194 | T108 | 98 | LGGSTLVNGG<u>T</u>WTRPHKAQVD 118 | 16 |
| gb\|AAF59929 | T132 | 122 | LGGSTLVNGG<u>T</u>WTRPHKAQVD 142 | 17 |
| gb\|ABG66642 | T108 | 98 | LGGSTLVNGG<u>T</u>WTRPHKAQVD 118 | 18 |
| emb\|CAC12802 | T131 | 121 | LGGSTLVNGG<u>T</u>WTRPHKVQVD 141 | 19 |
| ref\|XP_001588502 | T130 | 120 | LGGSTLINGA<u>T</u>WTRPHKIQVD 140 | 20 |
| ref\|XP_001395420 | T163 | 153 | LGGSTLINGG<u>T</u>WTRPHKSQLD 173 | 21 |

* Databases: gb: GenBank; sp: Swissprot; ref: RefSeq; emb: EMBL; pdb: Protein Data Bank
** SEQ ID NOs represent the full-length sequence It is evident from Table 7 that Phe373 of SEQ ID NO:1 is conserved among the amino acid sequences listed in Table 7. Accordingly, one of skill in the art can easily identify the Phe residue corresponding to the Phe373 of SEQ ID NO:1 within the conserved region using any of commercially available software programs for sequence alignment, and understand that a GOx mutant is easily prepared by introducing modification on that Phe residue.

TABLE 7

| Origin* | Position of mutation | | | SEQ ID NO** |
|---|---|---|---|---|
| gb\|AAD01493 | F373 | 363 | AGAGQGQ--AVF<u>F</u>ANFTETFGDY 383 | 1 |
| gb\|ABM63225 | F373 | 363 | AGAGQGQ--AVF<u>F</u>ANFTETFGDY 383 | 2 |
| sp\|Q92452 | F373 | 363 | AGAGQGQ--AVF<u>F</u>ANFTETFGDY 383 | 3 |
| ref\|XP_002482295 | F404 | 394 | AGAGQGQ--AVF<u>F</u>ANFTETFGDY 414 | 4 |
| emb\|CAE47418 | F373 | 363 | AGTGQGQ--AVF<u>F</u>ANFTEVFGDY 383 | 5 |

TABLE 7-continued

| Origin* | Position of mutation | | SEQ ID NO** |
|---|---|---|---|
| ref\|XP_002563451 | F372 | 363 A-PGQGQ--AAYFANFTEVLGDH 382 | 6 |
| ref\|XP_001217613 | F397 | 387 AGFGQGQ--AVYFANFTETFGED 407 | 7 |
| ref\|XP_001215424 | F371 | 361 AGFGQGQ--AVYFANFTETFEED 381 | 8 |
| ref\|XP_001727544 | F374 | 364 SGAGQGQ--AVYFASFNETFGDY 384 | 9 |
| ref\|XP_002375824 | F374 | 364 SGAGQGQ--AVYFASFNETFGDY 384 | 10 |
| ref\|XP_001216461 | F374 | 364 TGAGQGQ--AVYFANFTETFGDH 384 | 11 |
| gb\|ADP03053 | F351 | 341 AGAGQGQ--AAWFATFNETFGDY 361 | 12 |
| gb\|ACR56326 | F373 | 363 AGAGQGQ--AAWFATFNETFGDY 383 | 13 |
| sp\|P13006 | F373 | 363 AGAGQGQ--AAWFATFNETFGDY 383 | 14 |
| gb\|ABG54443 | F349 | 339 AGAGQGQ--AAWFATFNETFGDY 359 | 15 |
| gb\|AAV68194 | F349 | 339 AGAGQGQ--AAWFATFNETFGDY 359 | 16 |
| gb\|AAF59929 | F373 | 363 AGAGQGQ--AAWFATFNETFGDY 383 | 17 |
| gb\|ABG66642 | F349 | 339 AGAGQGQ--AAWFATFNETLGDY 359 | 18 |
| emb\|CAC12802 | F372 | 362 AGAGQGQ--VAIFATFNETFGDY 382 | 19 |
| ref\|XP_001588502 | F373 | 363 LGYGQGQ--AIYFATFNETFGKY 383 | 20 |
| ref\|XP_001395420 | F422 | 412 EANGQGQ--AAYFATFAEIFGKD 432 | 21 |

* Databases: gb: GenBank; sp: Swissprot; ref: RefSeq; emb: EMBL; pdb: Protein Data Bank
** SEQ ID NOs represent the full-length sequence Example 5

Additional GOx Mutants

Additional GOx mutants derived from GOx of *P. amagasakiens* (GenBank® AADO1493) and *A. niger* (SwissProt P13006) were prepared and their enzyme activity was analyzed in the same manner as described in Examples 1-4. The ratio of GDH activity:GOx activity of each mutant are summarized in Tables 8a, 8b, 9a and 9b below, with the ratio of the wild-type GOx being 100%. The SEQ ID NOs of the amino acid sequences of each wild-type GOx are shown in Tables 6 and 7. Also the alignment of the amino acid sequences around the mutated positions are shown in Tables 10a-h.

TABLE 8a

1GPE (AADO1493)

| | | Dh/Ox Ratio vs Wild-Type | |
|---|---|---|---|
| | Type of Enzyme | 10 mM Glucose | 100 mM Glucose |
| | Wild type | 100% | 100% |
| Thr53 | Thr53Ser | 125% | — |
| Ile116 | Ile116Val | 101% | — |
| Ser132 | Ser132Ala | 839% | 1235% |
| | Ser132Thr | 95% | 93% |
| | Ser132Val | 1248% | 888% |
| | Ser132Cys | 508% | 817% |
| | Ser132Ile | 715% | 851% |
| Ile237 | Ile237Val | — | 182% |
| Val371 | Val371Thr | 118% | 113% |
| | Val371Ala | 111% | 107% |
| Phe373 | Phe373Leu | 246% | 231% |
| | Phe373Tyr | 171% | 165% |
| | Phe373Ala | 862% | 885% |

TABLE 8a-continued

1GPE (AADO1493)

| | | Dh/Ox Ratio vs Wild-Type | |
|---|---|---|---|
| | Type of Enzyme | 10 mM Glucose | 100 mM Glucose |
| Glu434 | Glu434Gln | 215% | 134% |
| Phe436 | Phe436Trp | — | 1365% |
| | Phe436Ala | 544% | 592% |
| | Phe436Leu | — | 127% |
| | Phe436Tyr | — | 783% |
| Trp448 | Trp448Ala | 1680% | 1440% |
| | Trp448Ile | — | 4382% |
| | Trp448Ser | — | 644% |
| Trp537 | Trp537Ala | 546% | 550% |

TABLE 8b

1GPE (AADO1493)

| | | Dh/Ox Ratio vs Wild-Type | |
|---|---|---|---|
| | Type of Enzyme | 10 mM Glucose | 100 mM Glucose |
| | Wild type | 100% | 100% |
| Phe373 | Phe373Met | — | 195% |
| | Phe373Trp | — | 111% |
| Phe436 | Phe436Met | — | 155% |
| | Phe436Glu | — | <no oxidase> |
| Trp448 | Trp448Val | — | 4011% |
| | Trp448Met | — | <no oxidase> |
| | Trp448Thr | — | 2290% |
| | Trp448Cys | — | 4427% |

TABLE 9a

1CF3 (P13006)

| | | Dh/Ox Ratio vs Wild-Type | |
|---|---|---|---|
| | Type of Enzyme | 10 mM Glucose | 100 mM Glucose |
| | Wild type | 100% | 100% |
| Thr132 | Thr132Ala | 403% | 537% |
| | Thr132Ser | 155% | 112% |
| | Thr132Val | 323% | 503% |
| | Thr132Trp | 545% | 416% |
| | Thr132Cys | 1013% | 875% |
| Thr134 | Thr134Ala | 373% | 445% |
| Phe237 | Phe237Ile | 142% | 120% |
| Ala371 | Ala371Val | 223% | 180% |
| Phe373 | Phe373Leu | 293% | 316% |
| | Phe373Tyr | 170% | 159% |
| | Phe373Met | 149% | 141% |
| | Phe373Asn | 235% | 206% |
| Trp448 | Trp448Ala | 488% | 610% |
| dbl mutant | Thr132Ala/Phe373Tyr | 928% | 1511% |
| dbl mutant | Thr132Ser/Phe373Leu | 633% | 794% |

TABLE 9b

1CF3 (P13006)

| | | Dh/Ox Ratio vs Wild-Type | |
|---|---|---|---|
| | Type of Enzyme | 10 mM Glucose | 100 mM Glucose |
| | Wild type | 100% | 100% |
| Thr134 | Thr134Ile | — | 300% |
| | Thr134Met | — | 170% |
| Phe237 | Phe237Ala | — | <no oxidase> |
| | Phe237Val | — | 210% |
| | Phe237Met | — | 280% |
| | Phe237Ser | — | 780% |
| | Phe237Asp | — | 1600% |
| | Phe237Leu | — | 170% |
| | Phe237Thr | — | 2900% |
| | Phe237Asn | — | 600% |
| | Phe237Arg | — | <no oxidase> |
| | Phe237Cys | — | 650% |
| Phe436 | Phe436Leu | — | 1760% |
| | Phe436Ile | — | 1818% |
| | Phe436Met | — | 140% |
| Trp448 | Trp448Gly | — | 819% |
| | Trp448Val | — | 11134% |
| | Trp448Leu | — | 7742% |
| | Trp448Ser | — | 426% |
| | Trp448Asn | — | 642% |
| | Trp448Asp | — | 4368% |
| | Trp448Lys | — | <no oxidase> |
| | Trp448Ile | — | 940% |
| | Trp448Met | — | 1100% |
| | Trp448Phe | — | 400% |
| | Trp448Thr | — | 310% |
| | Trp448Cys | — | 590% |
| | Trp448Gln | — | 680% |
| | Trp448Tyr | — | 270% |

TABLE 10a

Amino acid sequences around Thr535.

| Origin | Position of mutation | Amino acid sequences around mutated position(s) |
|---|---|---|
| gbAAD01493 | T53 | 43 YDYIIAGGGLTGLTVAAKLTE 63 |
| gbABM63225 | T53 | 43 YDYIIAGGGLTGLTVAAKLTE 63 |
| spQ92452 | T53 | 43 YDYIIAGGGLTGLTVAAKLTE 63 |
| refXP_002482295 | T84 | 74 YDYIIAGGGLTGLTVAAKLTE 94 |
| embCAE47418 | T53 | 43 YDYIIAGGGLTGLTVAAKLTE 63 |
| refXP_002563451 | T53 | 43 YDYVIAGGGLTGLTVAAKLSE 63 |
| refXP_001217613 | T77 | 67 FDYIIAGGGLTGLTVAAKLTE 87 |
| refXP_001215424 | T51 | 41 FDYIIAGGGLTGLTVAAKLTE 61 |
| refXP_001727544 | T53 | 43 FDYVIAGGGLTGLTVATKLTE 63 |
| refXP_002375824 | T53 | 43 FDYVIAGGGLTGLTVATKLTE 63 |
| refXP_001216461 | T53 | 43 VDYIIAGGGLTGLTVAAKLTE 63 |
| gbADP03053 | T30 | 20 VDYIIAGGGLTGLTTAARLTE 40 |
| gbACR56326 | T52 | 42 VDYIIAGGGLTGLTTAARLTE 62 |
| spP13006 | T52 | 42 VDYIIAGGGLTGLTTAARLTE 62 |
| gbABG54443 | T28 | 18 VDYIIAGGGLTGLTTAARLTE 38 |
| gbAAV68194 | T28 | 18 VDYIIAGGGLTGLTTAARLTE 38 |
| gbAAF59929 | T52 | 42 VDYIIAGGGLTGLTTAARLTE 62 |
| gbABG66642 | T28 | 18 VDYIIAGGGLTGLTTAARLTE 38 |

TABLE 10a-continued
Amino acid sequences around Thr535.

| Origin | Position of mutation | Amino acid sequences around mutated position(s) |
|---|---|---|
| embCAC12802 | T51 | 41 VDDIIAGGGL<u>T</u>GLTTAARLTE 61 |
| refXP_001588502 | T50 | 40 FDYIVAGGGL<u>T</u>GLTAAAILSK 60 |

TABLE 10b
Amino acid sequences around Ile116.

| Origin | Position of mutation | Amino acid sequences around mutated position(s) |
|---|---|---|
| gbAAD01493 | I116 | 106 VPL--INNRTNN<u>I</u>KAGKGLGGST 126 |
| gbABM63225 | I116 | 106 VPL--INNRTNN<u>I</u>KAGKGLGGST 126 |
| spQ92452 | I116 | 106 VPL--INNRTNN<u>I</u>KAGKGLGGST 126 |
| refXP_002482295 | I147 | 137 VPL--INNRTNN<u>I</u>KAGKGLGGST 157 |
| embCAE47418 | I116 | 106 VPL--INNRTSS<u>I</u>KSGKGLGGST 126 |
| refXP_002563451 | I116 | 106 VPL--INNRTGE<u>I</u>KSGLGLGGST 126 |
| refXP_001217613 | I140 | 130 VPL--INNRTDN<u>I</u>KSGKGLGGST 150 |
| refXP_001215424 | I114 | 104 VPL--INNRTDN<u>I</u>KSGKGLGGST 124 |
| refXP_001727544 | I117 | 106 VPLA-VNNRTEL<u>I</u>RSGNGLGGST 127 |
| refXP_002375824 | I117 | 106 VPLA-VNNRTEL<u>I</u>RSGNGLGGST 127 |
| refXP_001216461 | I117 | 106 VPMG-INNRTLD<u>I</u>KSGKGLGGST 127 |
| gbADP03053 | I94 | 83 VELA-TNNQTAL<u>I</u>RSGNGLGGST 104 |
| gbACR56326 | I116 | 105 VELA-TNNQTAL<u>I</u>RSGNGLGGST 126 |
| spP13006 | I116 | 105 VELA-TNNQTAL<u>I</u>RSGNGLGGST 126 |
| gbABG54443 | I92 | 81 VELA-TNNQTAL<u>I</u>RSGNGLGGST 102 |
| gbAAV68194 | I92 | 81 VELA-TNNQTAL<u>I</u>RSGNGLGGST 102 |
| gbAAF59929 | I116 | 105 VELA-TNNQTAL<u>I</u>RSGNGLGGST 126 |
| gbABG66642 | I92 | 81 VELA-TNNQTAL<u>I</u>RSGNGLGGSS 102 |
| embCAC12802 | I115 | 104 VELA-TNNLTEL<u>I</u>RSGNGLGGST 125 |
| refXP_001588502 | I114 | 103 LNQT-ADIPQQT<u>I</u>RSGRGLGGST 124 |

TABLE 10c
Amino acid sequences around S/T132, W133 and T134.

| Origin | Position of mutation | Amino acid sequences around mutated position(s) |
|---|---|---|
| gbAAD01493 | S132, W133, T134 | 122 LGGSTLINGD<u>SWT</u>RPDKVQID 142 |
| gbABM63225 | S132, W133, T134 | 122 LGGSTLINGD<u>SWT</u>RPDKVQID 142 |
| spQ92452 | S132, W133, T134 | 122 LGGSTLINGD<u>SWT</u>RPDKVQID 142 |
| refXP_002482295 | S163, W164, T165 | 153 LGGSTLINGD<u>SWT</u>RPDKIQID 173 |
| embCAE47418 | S132, W133, T134 | 122 LGGSTLINGD<u>SWT</u>RPDKVQID 142 |
| refXP_002563451 | S132, W133, T134 | 122 LGGSTLINGD<u>SWT</u>RPDKVQID 142 |
| refXP_001217613 | S156, W157, T158 | 146 LGGSTLINGD<u>SWT</u>RPDKVQID 166 |
| refXP_001215424 | S130, W131, T132 | 120 LGGSTLINGD<u>SWT</u>RPDKVQID 140 |
| refXP_001727544 | S133, W134, T135 | 123 LGGSTLINGG<u>SWT</u>RPDKVQID 143 |
| refXP_002375824 | S133, W134, T135 | 123 LGGSTLINGG<u>SWT</u>RPDKVQID 143 |
| refXP_001216461 | S133, W134, T135 | 123 LGGSTLVNGG<u>SWT</u>SPDKVQLD 143 |
| gbADP03053 | T110, W111, T112 | 100 LGGSTLVNGG<u>TWT</u>RPHKAQVD 120 |
| gbACR56326 | T132, W133, T134 | 122 LGGSTLVNGG<u>TWT</u>RPHKAQVD 142 |
| spP13006 | T132, W133, T134 | 122 LGGSTLVNGG<u>TWT</u>RPHKAQVD 142 |
| gbABG54443 | T108, W109, T110 | 98 LGGSTLVNGG<u>TWT</u>RPHKAQVD 118 |

TABLE 10c-continued

Amino acid sequences around S/T132, W133 and T134.

| Origin | Position of mutation | muta-Amino acid sequences around mutated position(s) |
|---|---|---|
| gbAAV68194 | T108, W109, T110 | 98 LGGSTLVNGGTWTRPHKAQVD 118 |
| gbAAF59929 | T132, W133, T134 | 122 LGGSTLVNGGTWTRPHKAQVD 142 |
| gbABG66642 | T108, W109, T110 | 98 LGGSSLVNGGTWTRPHKAQVD 118 |
| embCAC12802 | T131, W132, T133 | 121 LGGSTLVNGGTWTRPHKVQVD 141 |
| refXP_001588502 | T130, W131, T132 | 120 LGGSTLINGATWTRPHKIQVD 140 |

TABLE 10d

Amino acid sequences around I/F237.

| Origin | Position of mutation | muta-Amino acid sequences around mutated position(s) |
|---|---|---|
| gbAAD01493 | I237 | 227 LCGHPRGVSMIMNNLDE--NQVR 247 |
| gbABM63225 | I237 | 227 LCGHPRGVSMIMNNLDE--NQVR 247 |
| spQ92452 | I237 | 227 LCGHPRGVSMIMNNVDE--NQVR 247 |
| refXP_002482295 | I268 | 258 LCGHPRGVSMIMNNVDE--NQVR 278 |
| embCAE47418 | I237 | 227 LCGHPRGVSMIYNNLDE--NQVR 247 |
| refXP_002563451 | I237 | 227 HCGHPRGVSMIPNNLHE--NQIR 247 |
| refXP_001217613 | I261 | 251 HCGHPRGVSMIPNNLLE--DQVR 271 |
| refXP_001215424 | I235 | 225 HCGHPRGVSMIPNNLLE--DQVR 245 |
| refXP_001727544 | I238 | 228 HCGHPRGVSMIPNAVHE--DQTR 248 |
| refXP_002375824 | I238 | 228 HCGHPRGVSMIPNAVHE--DQTR 248 |
| refXP_001216461 | I238 | 228 HCGHPRGVSMILNSLHE--DQTR 248 |
| gbADP03053 | F215 | 205 GCGDPHGVSMFPNTLHE--DQVR 225 |
| gbACR56326 | F237 | 227 GCGDPHGVSMFPNTLHE--DQVR 247 |
| spP13006 | F237 | 227 GCGDPHGVSMFPNTLHE--DQVR 247 |
| gbABG54443 | F213 | 203 GCGDPHGVSMFPNTLHE--DQVR 223 |
| gbAAV68194 | F213 | 203 GCGDPHGVSMFPNTLHE--DQVR 223 |
| gbAAF59929 | F237 | 227 GCGDPHGVSMFPNTLHE--DQVR 247 |
| gbABG66642 | F213 | 203 GCGDPHGVSMFPNTLHE--DQVR 223 |
| embCAC12802 | F236 | 226 GCGDPHGVSMFPNTLHE--DQVR 246 |
| refXP_001588502 | F235 | 225 SCGNPHGVSMFPNSLHANWNQTR 247 |

TABLE 10e

Amino acid sequences around V/A/I371 and F373.

| Origin | Position of mutation | muta-Amino acid sequences around mutated position(s) |
|---|---|---|
| gbAAD01493 | V371, F373 | 363 AGAGQGQ--AVFFANFTETFGDY 383 |
| gbABM63225 | V371, F373 | 363 AGAGQGQ--AVFFANFTETFGDY 383 |
| spQ92452 | V371, F373 | 363 AGAGQGQ--AVFFANFTETFGDY 383 |
| refXP_002482295 | V402, F404 | 394 AGAGQGQ--AVFFANFTETFGDY 414 |
| embCAE47418 | V371, F373 | 363 AGTGQGQ--AVFFANFTEVFGDY 383 |
| refXP_002563451 | A370, F372 | 363 A-PGQGQ--AAYFANFTEVLGDH 382 |
| refXP_001217613 | V395, F397 | 387 AGFGQGQ--AVYFANFTETFG ED 407 |
| refXP_001215424 | V369, F371 | 361 AGFGQGQ--AVYFANFTETFEED 381 |
| refXP_001727544 | V372, F374 | 364 SGAGQGQ--AVYFASFNETFGDY 384 |
| refXP_002375824 | V372, F374 | 364 SGAGQGQ--AVYFASFNETFGDY 384 |
| refXP_001216461 | V372, F374 | 364 TGAGQGQ--AVYFANFTETFGDH 384 |
| gbADP03053 | A349, F351 | 341 AGAGQGQ--AAWFATFNETFGDY 361 |
| gbACR56326 | A371, F373 | 363 AGAGQGQ--AAWFATFNETFGDY 383 |
| spP13006 | A371, F373 | 363 AGAGQGQ--AAWFATFNETFGDY 383 |
| gbABG54443 | A347, F349 | 339 AGAGQGQ--AAWFATFNETFGDY 359 |
| gbAAV68194 | A347, F349 | 339 AGAGQGQ--AAWFATFNETFGDY 359 |
| gbAAF59929 | A371, F373 | 363 AGAGQGQ--AAWFATFNETFGDY 383 |
| gbABG66642 | A347, F349 | 339 AGAGQGQ--AAWFATFNETLGDY 359 |
| embCAC12802 | A370, F372 | 362 AGAGQGQ--VAIFATFNETFGDY 382 |
| refXP_001588502 | I371, F373 | 363 LGYGQGQ--AIYFATFNETFGKY 383 |

TABLE 10f

Amino acid sequences around E434 and F436.

| Origin | Position of mutation | Amino acid sequences around mutated position(s) |
|---|---|---|
| gbAAD01493 | E434,426 F436 | LDED--VAFA<u>E</u>L<u>F</u>MDT--EGKINFD 446 |
| gbABM63225 | E434,426 F436 | LDED--VAFA<u>E</u>L<u>F</u>MDT--EGKINFD 446 |
| spQ92452 | E434,426 F436 | LDED--VAFA<u>E</u>L<u>F</u>MDT--EGKINFD 446 |
| refXP_002482295 | E435,457 F467 | LDED--VAFA<u>E</u>L<u>F</u>MDT--EGKINFD 477 |
| embCAE47418 | E434,426 F436 | LEED--VAYA<u>E</u>L<u>F</u>MDT--SGKINFD 446 |
| refXP_002563451 | E433,425 F435 | LDED--VAFA<u>E</u>L<u>F</u>FDT--EGKINFD 445 |
| refXP_001217613 | E458,450 F460 | LNED--VAYA<u>E</u>L<u>F</u>LDT--SGQINFD 470 |
| refXP_001215424 | E432,424 F434 | LNED--VAYA<u>E</u>L<u>F</u>LDT--SGQINFD 444 |
| refXP_001727544 | E435,427 F437 | LNED--VAFA<u>E</u>L<u>F</u>LDT--EGKINFD 447 |
| refXP_002375824 | E435,427 F437 | LNED--VAFA<u>E</u>L<u>F</u>LDT--EGKINFD 447 |
| refXP_001216461 | E435,427 F437 | LEDD--VAFV<u>E</u>F<u>F</u>FDS--NGMINFD 447 |
| gbADP03053 | E412,404 F414 | VNHN--VAYS<u>E</u>L<u>F</u>LDT--AGVASFD 424 |
| gbACR56326 | E434,426 F436 | VKDN--VAYS<u>E</u>L<u>F</u>LDT--AGVASFD 446 |
| spP13006 | E434,426 F436 | VNHN--VAYS<u>E</u>L<u>F</u>LDT--AGVASFD 446 |
| gbABG54443 | E410,402 F412 | VKDN--VAYS<u>E</u>L<u>F</u>LDT--AGVASFD 422 |
| gbAAV68194 | E410,402 F412 | VKDN--VAYS<u>E</u>L<u>F</u>LDT--AGVASFD 422 |
| gbAAF59929 | E434,426 F436 | VNHN--VAYS<u>E</u>L<u>F</u>LDT--AGVASFD 446 |
| gbABG66642 | E410,402 F412 | VKDN--VAYS<u>E</u>L<u>F</u>LDT--AGVASFG 422 |
| embCAC12802 | E433,425 F435 | VNHN--VAYS<u>E</u>L<u>F</u>LDT--AGAVSFT 445 |
| refXP_001588502 | E434,426 F436 | TKDN--IAYS<u>E</u>L<u>F</u>MDT--EGAINFD 446 |

TABLE 10g

Amino acid sequences around W448.

| Origin | Position of mutation | Amino acid sequences around mutated position(s) |
|---|---|---|
| gbAAD01493 | W448 | 438 DT--EGKINFDL<u>W</u>DLIPFTRGSV 458 |
| gbABM63225 | W448 | 438 DT--EGKINFDL<u>W</u>DLIPFTRGSV 458 |
| spQ92452 | W448 | 438 DT--EGKINFDL<u>W</u>DLIPFTRGSV 458 |
| refXP_002482295 | W479 | 469 DT--EGKINFDL<u>W</u>DLIPFTRGSV 489 |
| embCAE47418 | W448 | 438 DT--SGKINFDL<u>W</u>DLIPFTRGSV 458 |
| refXP_002563451 | W447 | 437 DT--EGKINFDI<u>W</u>NLIPFTRGSV 457 |
| refXP_001217613 | W472 | 462 DT--SGQINFDL<u>W</u>DLIPFTRGST 482 |
| refXP_001215424 | W446 | 436 DT--SGQINFDL<u>W</u>DLIPFTRGST 456 |
| refXP_001727544 | W449 | 439 DT--EGKINFDL<u>W</u>DLIPFTRGSV 459 |
| refXP_002375824 | W449 | 439 DT--EGKINFDL<u>W</u>DLIPFTRGSV 459 |
| refXP_001216461 | W449 | 439 DS--NGMINFDL<u>W</u>DLIPFTRGST 459 |
| gbADP03053 | W426 | 416 DT--AGVASFDV<u>W</u>DLLPFTRGYV 436 |
| gbACR56326 | W448 | 438 DT--AGVASFDV<u>W</u>DLLPFTRGYV 458 |
| spP13006 | W448 | 438 DT--AGVASFDV<u>W</u>DLLPFTRGYV 458 |
| gbABG54443 | W424 | 414 DT--AGVASFDV<u>W</u>DLLPFTRGYV 434 |
| gbAAV68194 | W424 | 414 DT--AGVASFDV<u>W</u>DLLPFTRGYV 434 |
| gbAAF59929 | W448 | 438 DT--AGVASFDV<u>W</u>DLLPFDRGYV 458 |
| gbABG66642 | W424 | 414 DT--AGVASFGV<u>W</u>DLLPFTRGYV 434 |
| embCAC12802 | W447 | 437 DT--AGAVSFTI<u>W</u>DLIPFTRGYV 457 |
| refXP_001588502 | W448 | 438 DT--EGAINFDL<u>W</u>TLIPFTRGFV 458 |

TABLE 10h

Amino acid sequences around W/Y537.

| Origin | Position of mutation | Amino acid sequences around mutated position(s) |
|---|---|---|
| gbAAD01493 | W537 | 527 DYVLQN-FRPN<u>W</u>HAVSSCSMMS 547 |
| gbABM63225 | W537 | 527 DYVLQN-FRPN<u>W</u>HAVSSCSMMS 547 |
| spQ92452 | W537 | 527 DYVLQN-FRPN<u>W</u>HAVSSCSMMS 547 |
| refXP_002482295 | W568 | 558 AYVLQN-FRPN<u>W</u>HAVSSCSMMS 578 |
| embCAE47418 | W537 | 527 DYVIQN-FRPN<u>W</u>HAVSSCSMMA 547 |
| refXP_002563451 | W536 | 526 DYVMMN-FRPN<u>W</u>HAVSTCSMMS 546 |
| refXP_001217613 | W561 | 551 EYVKDN-FRAN<u>W</u>HAVGTCSMMS 571 |
| refXP_001215424 | W535 | 525 EYVKDN-FRAN<u>W</u>HAVGTCSMMS 545 |
| refXP_001727544 | W538 | 528 DYVKEN-FRAN<u>W</u>HAVSSCSMMS 548 |
| refXP_002375824 | W538 | 528 DYVKEN-FRAN<u>W</u>HAVSSCSMMS 548 |

TABLE 10h-continued

Amino acid sequences around W/Y537.

| Origin | Position of mutation | Amino acid sequences around mutated position(s) |
|---|---|---|
| refXP_001216461 | W539 529 | EYVKQN-FRANWHAVSTCAMMS 549 |
| gbADP03053 | Y515 505 | EYIPYH-FRPNYHGVGTCSMMP 525 |
| gbACR56326 | Y537 527 | EYIPYN-FRPNYHGVGTCSMMP 547 |
| spP13006 | Y537 527 | EYIPYH-FRPNYHGVGTCSMMP 547 |
| gbABG54443 | Y513 503 | EYIPYN-FRPNYHGVGTCSMMP 523 |
| gbAAV68194 | Y513 503 | EYIPYN-FRPNYHGVGTCSMMP 523 |
| gbAAF59929 | Y537 527 | EYIPYH-FRPNYHDVGTCSMMP 547 |
| gbABG66642 | Y513 503 | EYIPYN-FRPNYHGVGTCSMMP 523 |
| embCAC12802 | Y536 526 | EYIKYN-FRPNYHGVGTCSMMK 546 |
| refXP_001588502 | Y538 528 | SYVKQN-FRPNYHNVGSCSMMA 548 |

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A glucose oxidase mutant modified at one or more amino acid positions selected from:
   (a). a position corresponding to position 53 of the amino acid sequence set forth in SEQ ID NO: 1 by substituting the amino acid residue Thr with another amino acid residue;
   (b). a position corresponding to position 116 of the amino acid sequence set forth in SEQ ID NO: 1 by substituting the amino acid residue Ile with another amino acid residue;
   (c). a position corresponding to position 132 of the amino acid sequence set forth in SEQ ID NO: 1 by substituting the amino acid residue Ser or Thr with another amino acid residue;
   (d). a position corresponding to position 134 of the amino acid sequence set forth in SEQ ID NO: 1 by substituting the amino acid residue Thr with another amino acid residue;
   (e). a position corresponding to position 237 of the amino acid sequence set forth in SEQ ID NO: 1 by substituting the amino acid residue Ile or Phe with another amino acid residue;
   (f). a position corresponding to position 371 of the amino acid sequence set forth in SEQ ID NO: 1 by substituting the amino acid residue Val or Ala with another amino acid residue;
   (g). a position corresponding to position 373 of the amino acid sequence set forth in SEQ ID NO: 1 by substituting the amino acid residue Phe with another amino acid residue;
   (h). a position corresponding to position 434 of the amino acid sequence set forth in SEQ ID NO: 1 by substituting the amino acid residue Glu with another amino acid residue;
   (i). a position corresponding to position 436 of the amino acid sequence set forth in SEQ ID NO: 1 by substituting the amino acid residue Phe with another amino acid residue;
   (j). a position corresponding to position 448 of the amino acid sequence set forth in SEQ ID NO: 1 by substituting the amino acid residue Trp with another amino acid residue; and
   (k). a position corresponding to position 537 of the amino acid sequence set forth in SEQ ID NO: 1 by substituting the amino acid residue Trp with another amino acid residue.

2. The glucose oxidase mutant of claim 1, wherein the glucose oxidase mutant is modified at one or more positions selected from:
   (a). the position corresponding to position 53 of the amino acid sequence set forth in SEQ ID NO: 1 by substituting the amino acid residue Thr with Ser;
   (b). the position corresponding to position 116 of the amino acid sequence set forth in SEQ ID NO: 1 by substituting the amino acid residue Ile with Val;
   (c). the position corresponding to position 132 of the amino acid sequence set forth in SEQ ID NO: 1 by substituting the amino acid residue Ser with Ala, Thr, Val, Cys or Ile, or by substituting the amino acid residue Thr with Ala, Ser, Val, Trp or Cys;

(d). the position corresponding to position 134 of the amino acid sequence set forth in SEQ ID NO: 1 by substituting the amino acid residue Thr with Ala, Ile or Met;

(e). the position corresponding to position 237 of the amino acid sequence set forth in SEQ ID NO: 1 by substituting the amino acid residue Ile with Val, or by substituting the amino acid residue Phe with Ile, Ala, Val, Met, Ser, Asp, Leu, Thr, Asn, Arg or Cys;

(f). the position corresponding to position 371 of the amino acid sequence set forth in SEQ ID NO: 1 by substituting the amino acid residue Val with Thr, Ala, or by substituting the amino acid residue Ala with Val;

(g). the position corresponding to position 373 of the amino acid sequence set forth in SEQ ID NO: 1 by substituting the amino acid residue Phe with Leu, Tyr, Ala, Met, Asn or Trp;

(h). the position corresponding to position 434 of the amino acid sequence set forth in SEQ ID NO: 1 by substituting the amino acid residue Glu with Gln;

(i). the position corresponding to position 436 of the amino acid sequence set forth in SEQ ID NO: 1 by substituting the amino acid residue Phe with Trp, Ala, Leu, Tyr, Met, Glu or Ile;

(j). the position corresponding to position 448 of the amino acid sequence set forth in SEQ ID NO: 1 by substituting the amino acid residue Trp with Ala, Ile, Ser, Val, Met, Thr, Cys, Gly, Leu, Asn, Asp, Lys, Phe, Gln or Tyr; and (k). the position corresponding to position 537 of the amino acid sequence set forth in SEQ ID NO: 1 by substituting the amino acid residue Trp with Ala.

3. The glucose oxidase mutant of claim 1, wherein the glucose oxidase mutant has a reduced oxidase activity when compared to a wild-type glucose oxidase.

4. The glucose oxidase mutant of claim 1, wherein the glucose oxidase mutant has an oxidase activity that is less than its dehydrogenase activity.

5. The glucose oxidase mutant of claim 1, wherein the glucose oxidase mutant has a dehydrogenase activity of about 50% or more of a wild-type glucose oxidase.

6. The glucose oxidase mutant of claim 1, wherein the glucose oxidase mutant has higher ratio of glucose dehydrogenase activity:glucose oxidase activity than that of a wild-type glucose oxidase.

7. The glucose oxidase mutant of claim 1, wherein the glucose oxidase mutant has an amino acid sequence selected from the group consisting of SEQ ID NOs: 1-21, modified at one or more positions corresponding to position 53, 116, 132, 134, 237, 371, 373, 434, 436, 448 or 537 of the amino acid sequence set forth in SEQ ID NO: 1.

8. A glucose oxidase mutant comprising an amino acid sequence selected from the group consisting of SEQ ID NOs: 1-21 modified at one or more positions corresponding to position 53, 116, 132, 134, 237, 371, 373, 434, 436, 448 or 537 of the amino acid sequence set forth in SEQ ID NO: 1, wherein the glucose oxidase mutant has a reduced oxidase activity when compared to a wild-type glucose oxidase.

9. An isolated polynucleotide encoding the glucose oxidase mutant of claim 1.

10. A vector comprising the polynucleotide of claim 9.

11. A host cell transformed with the vector of claim 10.

12. A method of assaying glucose in a sample, the method comprising the steps of:

contacting the sample with a glucose oxidase mutant modified at one or more amino acid positions selected from:

(a). a position corresponding to position 53 of the amino acid sequence set forth in SEQ ID NO: 1 by substituting the amino acid residue Thr with another amino acid residue, (b). a position corresponding to position 116 of the amino acid sequence set forth in SEQ ID NO: 1 by substituting the amino acid residue Ile with another amino acid residue, (c). a position corresponding to position 132 of the amino acid sequence set forth in SEQ ID NO: 1 by substituting the amino acid residue Ser or Thr with another amino acid residue, (d). a position corresponding to position 134 of the amino acid sequence set forth in SEQ ID NO: 1 by substituting the amino acid residue Thr with another amino acid residue, (e). a position corresponding to position 237 of the amino acid sequence set forth in SEQ ID NO: 1 by substituting the amino acid residue Ile or Phe with another amino acid residue, (f). a position corresponding to position 371 of the amino acid sequence set forth in SEQ ID NO: 1 by substituting the amino acid residue Val or Ala with another amino acid residue, (g). a position corresponding to position 373 of the amino acid sequence set forth in SEQ ID NO: 1 by substituting the amino acid residue Phe with another amino acid residue, (h). a position corresponding to position 434 of the amino acid sequence set forth in SEQ ID NO: 1 by substituting the amino acid residue Glu with another amino acid residue, (i). a position corresponding to position 436 of the amino acid sequence set forth in SEQ ID NO: 1 by substituting the amino acid residue Phe with another amino acid residue, (j). a position corresponding to position 448 of the amino acid sequence set forth in SEQ ID NO: 1 by substituting the amino acid residue Trp with another amino acid residue, and (k). a position corresponding to position 537 of the amino acid sequence set forth in SEQ ID NO: 1 by substituting the amino acid residue Trp with another amino acid residue; and measuring an amount of glucose oxidized by the glucose oxidase.

13. The method of claim 12, wherein the glucose oxidase mutant is modified at one or more positions selected from:

(a). the position corresponding to position 53 of the amino acid sequence set forth in SEQ ID NO: 1 by substituting the amino acid residue Thr with Ser;

(b). the position corresponding to position 116 of the amino acid sequence set forth in SEQ ID NO: 1 by substituting the amino acid residue Ile with Val;

(c). the position corresponding to position 132 of the amino acid sequence set forth in SEQ ID NO: 1 by substituting the amino acid residue Ser with Ala, Thr, Val, Cys or Ile, or by substituting the amino acid residue Thr with Ala, Ser, Val, Trp or Cys;

(d). the position corresponding to position 134 of the amino acid sequence set forth in SEQ ID NO: 1 by substituting the amino acid residue Thr with Ala, Ile or Met;

(e). the position corresponding to position 237 of the amino acid sequence set forth in SEQ ID NO: 1 by substituting the amino acid residue Ile with Val, or by substituting the amino acid residue Phe with Ile, Ala, Val, Met, Ser, Asp, Leu, Thr, Asn, Arg or Cys;

(f). the position corresponding to position 371 of the amino acid sequence set forth in SEQ ID NO: 1 by substituting the amino acid residue Val with Thr, Ala, or by substituting the amino acid residue Ala with Val;

(g). the position corresponding to position 373 of the amino acid sequence set forth in SEQ ID NO: 1 by substituting the amino acid residue Phe with Leu, Tyr, Ala, Met, Asn or Trp;

(h). the position corresponding to position 434 of the amino acid sequence set forth in SEQ ID NO: 1 by substituting the amino acid residue Glu with Gln;

(i). the position corresponding to position 436 of the amino acid sequence set forth in SEQ ID NO: 1 by substituting the amino acid residue Phe with Trp, Ala, Leu, Tyr, Met, Glu or Ile;

(j). the position corresponding to position 448 of the amino acid sequence set forth in SEQ ID NO: 1 by substituting the amino acid residue Trp with Ala, Ile, Ser, Val, Met, Thr, Cys, Gly, Leu, Asn, Asp, Lys, Phe, Gln or Tyr; and (k). the position corresponding to position 537 of the amino acid sequence set forth in SEQ ID NO: 1 by substituting the amino acid residue Trp with Ala.

14. A device for assaying glucose in a sample, the device comprising:
   the glucose oxidase of claim 1; and
   an electron mediator.

15. A kit for assaying glucose in a sample, the kit comprising:
   glucose oxidase of claim 1; and
   an electron mediator.

16. An enzyme electrode comprising the glucose oxidase of claim 1 immobilized on an electrode.

17. An enzyme sensor for assaying glucose comprising the enzyme electrode of claim 16 as a working electrode.

* * * * *

SEQUENCE LISTING

```
<160> NUMBER OF SEQ ID NOS: 33

<210> SEQ ID NO 1
<211> LENGTH: 605
<212> TYPE: PRT
<213> ORGANISM: Penicillium amagasakiense
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Ser, then Xaa373 is not Phe

<400> SEQUENCE: 1

Met Val Ser Val Phe Leu Ser Thr Leu Leu Leu Ser Ala Ala Ala Val
1               5                   10                  15

Gln Ala Tyr Leu Pro Ala Gln Gln Ile Asp Val Gln Ser Ser Leu Leu
            20                  25                  30

Ser Asp Pro Ser Lys Val Ala Gly Lys Thr Tyr Asp Tyr Ile Ile Ala
        35                  40                  45

Gly Gly Gly Leu Thr Gly Leu Thr Val Ala Ala Lys Leu Thr Glu Asn
    50                  55                  60

Pro Lys Ile Lys Val Leu Val Ile Glu Lys Gly Phe Tyr Glu Ser Asn
65                  70                  75                  80

Asp Gly Ala Ile Ile Glu Asp Pro Asn Ala Tyr Gly Gln Ile Phe Gly
                85                  90                  95

Thr Thr Val Asp Gln Asn Tyr Leu Thr Val Pro Leu Ile Asn Asn Arg
            100                 105                 110

Thr Asn Asn Ile Lys Ala Gly Lys Gly Leu Gly Gly Ser Thr Leu Ile
        115                 120                 125

Asn Gly Asp Xaa Trp Thr Arg Pro Asp Lys Val Gln Ile Asp Ser Trp
    130                 135                 140

Glu Lys Val Phe Gly Met Glu Gly Trp Asn Trp Asp Asn Met Phe Glu
```

-continued

```
            145                 150                 155                 160
Tyr Met Lys Lys Ala Glu Ala Ala Arg Thr Pro Thr Ala Ala Gln Leu
                    165                 170                 175

Ala Ala Gly His Ser Phe Asn Ala Thr Cys His Gly Thr Asn Gly Thr
                    180                 185                 190

Val Gln Ser Gly Ala Arg Asp Asn Gly Gln Pro Trp Ser Pro Ile Met
                    195                 200                 205

Lys Ala Leu Met Asn Thr Val Ser Ala Leu Gly Val Pro Val Gln Gln
                    210                 215                 220

Asp Phe Leu Cys Gly His Pro Arg Gly Val Ser Met Ile Met Asn Asn
225                 230                 235                 240

Leu Asp Glu Asn Gln Val Arg Val Asp Ala Arg Ala Trp Leu Leu
                    245                 250                 255

Pro Asn Tyr Gln Arg Ser Asn Leu Glu Ile Leu Thr Gly Gln Met Val
                    260                 265                 270

Gly Lys Val Leu Phe Lys Gln Thr Ala Ser Gly Pro Gln Ala Val Gly
                    275                 280                 285

Val Asn Phe Gly Thr Asn Lys Ala Val Asn Phe Asp Val Phe Ala Lys
                    290                 295                 300

His Glu Val Leu Leu Ala Ala Gly Ser Ala Ile Ser Pro Leu Ile Leu
305                 310                 315                 320

Glu Tyr Ser Gly Ile Gly Leu Lys Ser Val Leu Asp Gln Ala Asn Val
                    325                 330                 335

Thr Gln Leu Leu Asp Leu Pro Val Gly Ile Asn Met Gln Asp Gln Thr
                    340                 345                 350

Thr Thr Thr Val Ser Ser Arg Ala Ser Ser Ala Gly Ala Gly Gln Gly
                    355                 360                 365

Gln Ala Val Phe Xaa Ala Asn Phe Thr Glu Thr Phe Gly Asp Tyr Ala
                    370                 375                 380

Pro Gln Ala Arg Asp Leu Leu Asn Thr Lys Leu Asp Gln Trp Ala Glu
385                 390                 395                 400

Glu Thr Val Ala Arg Gly Gly Phe His Asn Val Thr Ala Leu Lys Val
                    405                 410                 415

Gln Tyr Glu Asn Tyr Arg Asn Trp Leu Leu Asp Glu Asp Val Ala Phe
                    420                 425                 430

Ala Glu Leu Phe Met Asp Thr Glu Gly Lys Ile Asn Phe Asp Leu Trp
                    435                 440                 445

Asp Leu Ile Pro Phe Thr Arg Gly Ser Val His Ile Leu Ser Ser Asp
450                 455                 460

Pro Tyr Leu Trp Gln Phe Ala Asn Asp Pro Lys Phe Phe Leu Asn Glu
465                 470                 475                 480

Phe Asp Leu Leu Gly Gln Ala Ala Ser Lys Leu Ala Arg Asp Leu
                    485                 490                 495

Thr Ser Gln Gly Ala Met Lys Glu Tyr Phe Ala Gly Glu Thr Leu Pro
                    500                 505                 510

Gly Tyr Asn Leu Val Gln Asn Ala Thr Leu Ser Gln Trp Ser Asp Tyr
                    515                 520                 525

Val Leu Gln Asn Phe Arg Pro Asn Trp His Ala Val Ser Ser Cys Ser
                    530                 535                 540

Met Met Ser Arg Glu Leu Gly Gly Val Val Asp Ala Thr Ala Lys Val
545                 550                 555                 560

Tyr Gly Thr Gln Gly Leu Arg Val Ile Asp Gly Ser Ile Pro Pro Thr
                    565                 570                 575
```

```
Gln Val Ser Ser His Val Met Thr Ile Phe Tyr Gly Met Ala Leu Lys
            580                 585                 590

Val Ala Asp Ala Ile Leu Asp Asp Tyr Ala Lys Ser Ala
        595                 600                 605

<210> SEQ ID NO 2
<211> LENGTH: 605
<212> TYPE: PRT
<213> ORGANISM: Penicillium adametzii
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Ser, then Xaa373 is not Phe

<400> SEQUENCE: 2

Met Val Ser Val Phe Leu Ser Thr Leu Leu Ser Ala Ala Thr Val
1               5                   10                  15

Gln Ala Tyr Leu Pro Ala Gln Gln Ile Asp Val Gln Ser Ser Leu Leu
            20                  25                  30

Ser Asp Pro Ser Lys Val Ala Gly Lys Thr Tyr Asp Tyr Ile Ile Ala
            35                  40                  45

Gly Gly Gly Leu Thr Gly Leu Thr Val Ala Ala Lys Leu Thr Glu Asn
        50                  55                  60

Pro Lys Ile Lys Val Leu Val Ile Glu Lys Gly Phe Tyr Glu Ser Asn
65                  70                  75                  80

Asp Gly Ala Ile Ile Glu Asp Pro Asn Ala Tyr Gly Gln Ile Phe Gly
                85                  90                  95

Thr Thr Val Asp Gln Asn Tyr Leu Thr Val Pro Leu Ile Asn Asn Arg
            100                 105                 110

Thr Asn Asn Ile Lys Ala Gly Lys Gly Leu Gly Gly Ser Thr Leu Ile
        115                 120                 125

Asn Gly Asp Xaa Trp Thr Arg Pro Asp Lys Val Gln Ile Asp Ser Trp
    130                 135                 140

Glu Lys Val Phe Gly Met Glu Gly Trp Asn Trp Asp Asn Met Phe Glu
145                 150                 155                 160

Tyr Met Lys Lys Ala Glu Ala Ala Arg Thr Pro Thr Ala Ala Gln Val
                165                 170                 175

Ala Ala Gly His Ser Phe Asn Ala Thr Cys His Gly Thr Asn Gly Thr
            180                 185                 190

Val Gln Ser Gly Ala Arg Asp Asn Gly Gln Pro Trp Ser Pro Ile Met
        195                 200                 205

Lys Ala Leu Met Asn Thr Val Ser Ala Leu Gly Val Pro Val Gln Gln
    210                 215                 220

Asp Phe Leu Cys Gly His Pro Arg Gly Val Ser Met Ile Met Asn Asn
225                 230                 235                 240

Leu Asp Glu Asn Gln Val Arg Val Asp Ala Ala Arg Ala Trp Leu Leu
                245                 250                 255

Pro Asn Tyr Gln Arg Pro Asn Leu Glu Ile Leu Thr Gly Gln Met Val
            260                 265                 270

Gly Lys Val Leu Phe Lys Gln Thr Ala Ser Gly Pro Gln Ala Val Gly
        275                 280                 285
```

```
Val Asn Phe Gly Thr Asn Lys Ala Val Asn Phe Asp Val Phe Ala Lys
        290                 295                 300

His Glu Val Leu Leu Ala Ala Gly Ser Ala Ile Ser Pro Leu Ile Leu
305                 310                 315                 320

Glu Tyr Ser Gly Ile Gly Leu Lys Ser Val Leu Asp Gln Ala Asn Val
                325                 330                 335

Thr Gln Leu Leu Asp Leu Pro Val Gly Ile Asn Met Gln Asp Gln Thr
            340                 345                 350

Thr Thr Thr Val Ser Ser Arg Ala Ser Ala Ala Gly Ala Gly Gln Gly
            355                 360                 365

Gln Ala Val Phe Xaa Ala Asn Phe Thr Glu Thr Phe Gly Asp Tyr Ala
370                 375                 380

Pro Gln Ala Arg Asp Leu Leu Asn Thr Lys Leu Asp Gln Trp Ala Glu
385                 390                 395                 400

Glu Thr Val Ala Arg Gly Gly Phe His Asn Val Thr Ala Leu Lys Val
                405                 410                 415

Gln Tyr Glu Asn Tyr Arg Asn Trp Leu Leu Asp Glu Asp Val Ala Phe
            420                 425                 430

Ala Glu Leu Phe Met Asp Thr Glu Gly Lys Ile Asn Phe Asp Leu Trp
            435                 440                 445

Asp Leu Ile Pro Phe Thr Arg Gly Ser Val His Ile Leu Ser Ser Asp
450                 455                 460

Pro Tyr Leu Trp Gln Phe Ala Asn Asp Pro Lys Phe Phe Leu Asn Glu
465                 470                 475                 480

Phe Asp Leu Leu Gly Gln Ala Ala Ala Ser Lys Leu Ala Arg Asp Leu
                485                 490                 495

Thr Ser Gln Gly Ala Met Lys Glu Tyr Phe Ala Gly Glu Thr Leu Pro
            500                 505                 510

Gly Tyr Asn Leu Val Gln Asn Ala Thr Leu Ser Gln Trp Ser Asp Tyr
            515                 520                 525

Val Leu Gln Asn Phe Arg Pro Asn Trp His Ala Val Ser Ser Cys Ser
530                 535                 540

Met Met Ser Arg Glu Leu Gly Gly Val Val Asp Ala Thr Ala Lys Val
545                 550                 555                 560

Tyr Gly Thr Gln Gly Leu Arg Val Ile Asp Gly Ser Ile Pro Pro Thr
                565                 570                 575

Gln Val Ser Ser His Val Met Thr Ile Phe Tyr Gly Met Ala Leu Lys
            580                 585                 590

Val Ala Asp Ala Ile Leu Asp Asp Tyr Ala Lys Ser Ala
            595                 600                 605

<210> SEQ ID NO 3
<211> LENGTH: 605
<212> TYPE: PRT
<213> ORGANISM: Talaromyces flavus
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Ser, then Xaa373 is not Phe

<400> SEQUENCE: 3

Met Val Ser Val Phe Leu Ser Thr Leu Leu Leu Ala Ala Ala Thr Val
```

```
1               5                   10                  15
Gln Ala Tyr Leu Pro Ala Gln Gln Ile Asp Val Gln Ser Ser Leu Leu
                20                  25                  30
Ser Asp Pro Ser Lys Val Ala Gly Lys Thr Tyr Asp Tyr Ile Ile Ala
            35                  40                  45
Gly Gly Gly Leu Thr Gly Leu Thr Val Ala Ala Lys Leu Thr Glu Asn
        50                  55                  60
Pro Lys Ile Lys Val Leu Val Ile Glu Lys Gly Phe Tyr Glu Ser Asn
65                  70                  75                  80
Asp Gly Ala Ile Ile Glu Asp Pro Asn Ala Tyr Gly Gln Ile Phe Gly
                85                  90                  95
Thr Thr Val Asp Gln Asn Tyr Leu Thr Val Pro Leu Ile Asn Asn Arg
            100                 105                 110
Thr Asn Asn Ile Lys Ala Gly Lys Gly Leu Gly Gly Ser Thr Leu Ile
            115                 120                 125
Asn Gly Asp Xaa Trp Thr Arg Pro Asp Lys Val Gln Ile Asp Ser Trp
        130                 135                 140
Glu Lys Val Phe Gly Met Glu Gly Trp Asn Trp Asp Ser Met Phe Glu
145                 150                 155                 160
Tyr Met Lys Lys Ala Glu Ala Arg Ala Pro Thr Ala Ala Gln Leu
                165                 170                 175
Ala Ala Gly His Tyr Phe Asn Ala Thr Cys His Gly Thr Asn Gly Thr
            180                 185                 190
Val Gln Ser Gly Ala Arg Asp Asn Gly Gln Pro Trp Ser Pro Ile Met
            195                 200                 205
Lys Ala Leu Met Asn Thr Val Ser Ala Leu Gly Val Pro Val Gln Gln
        210                 215                 220
Asp Phe Leu Cys Gly His Pro Arg Gly Val Ser Met Ile Met Asn Asn
225                 230                 235                 240
Val Asp Glu Asn Gln Val Arg Val Asp Ala Ala Arg Ala Trp Leu Leu
                245                 250                 255
Pro Ser Tyr Gln Arg Pro Asn Leu Glu Ile Leu Thr Gly Gln Met Val
            260                 265                 270
Gly Lys Val Leu Phe Lys Gln Thr Ala Ser Gly Pro Gln Ala Val Gly
            275                 280                 285
Val Asn Phe Gly Thr Asn Lys Ala Val Asn Phe Asp Val Phe Ala Lys
        290                 295                 300
His Glu Val Leu Leu Ala Ala Gly Ser Ala Ile Ser Pro Leu Ile Leu
305                 310                 315                 320
Glu Tyr Ser Gly Ile Gly Leu Lys Ser Val Leu Asp Gln Ala Asn Val
                325                 330                 335
Thr Gln Leu Leu Asp Leu Pro Val Gly Ile Asn Met Gln Asp Gln Thr
            340                 345                 350
Thr Thr Thr Val Ser Ser Arg Ala Ser Ala Gly Ala Gly Gln Gly
            355                 360                 365
Gln Ala Val Phe Xaa Ala Asn Phe Thr Glu Thr Phe Gly Asp Tyr Ala
        370                 375                 380
Pro Gln Ala Arg Glu Leu Leu Asn Thr Lys Leu Asp Gln Trp Ala Glu
385                 390                 395                 400
Glu Thr Val Ala Arg Gly Gly Phe His Asn Val Thr Ala Leu Lys Val
                405                 410                 415
Gln Tyr Glu Asn Tyr Arg Asn Trp Leu Leu Asp Glu Asp Val Ala Phe
            420                 425                 430
```

-continued

```
Ala Glu Leu Phe Met Asp Thr Glu Gly Lys Ile Asn Phe Asp Leu Trp
        435                 440                 445

Asp Leu Ile Pro Phe Thr Arg Gly Ser Val His Ile Leu Ser Ser Asp
    450                 455                 460

Pro Tyr Leu Trp Gln Phe Ala Asn Asp Pro Lys Phe Phe Leu Asn Glu
465                 470                 475                 480

Phe Asp Leu Leu Gly Gln Ala Ala Ser Lys Leu Ala Arg Asp Leu
                485                 490                 495

Thr Ser Gln Gly Ala Met Lys Glu Tyr Phe Ala Gly Glu Thr Leu Pro
            500                 505                 510

Gly Tyr Asn Leu Val Glu Asn Ala Thr Leu Ser Gln Trp Ser Asp Tyr
        515                 520                 525

Val Leu Gln Asn Phe Arg Pro Asn Trp His Ala Val Ser Ser Cys Ser
    530                 535                 540

Met Met Ser Arg Glu Leu Gly Gly Val Val Asp Ala Thr Ala Lys Val
545                 550                 555                 560

Tyr Gly Thr Gln Gly Leu Arg Val Ile Asp Gly Ser Ile Pro Pro Thr
                565                 570                 575

Gln Val Ser Ser His Val Met Thr Ile Phe Tyr Gly Met Ala Leu Lys
            580                 585                 590

Val Ala Asp Ala Ile Leu Asp Asp Tyr Ala Lys Ser Ala
        595                 600                 605

<210> SEQ ID NO 4
<211> LENGTH: 636
<212> TYPE: PRT
<213> ORGANISM: Talaromyces stipitatus
<220> FEATURE:
<221> NAME/KEY: MISC_FEATURE
<222> LOCATION: (163)..(163)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (404)..(404)
<223> OTHER INFORMATION: Xaa is Phe, Ala, Leu, Trp or Tyr, provided that
      when Xaa163 is Ser, then Xaa404 is not Phe

<400> SEQUENCE: 4

Met Lys Gly Asn Val Cys Phe Leu Gln Val Tyr Lys Leu Ser Asp Ile
1               5                   10                  15

Tyr Arg Cys Ser Asp Lys Phe Phe Ser Thr Thr Ile Arg Ser Phe Thr
            20                  25                  30

Thr Leu Leu Ala Ile Pro Thr Leu Leu Phe Ser Ala Ala Thr Val Gln
        35                  40                  45

Ala Tyr Leu Pro Ala Glu Gln Ile Asp Val Gln Ser Ser Leu Leu Ser
    50                  55                  60

Glu Pro Ser Lys Val Ala Gly Lys Thr Tyr Asp Tyr Ile Ile Ala Gly
65                  70                  75                  80

Gly Gly Leu Thr Gly Leu Thr Val Ala Ala Lys Leu Thr Glu Asn Pro
                85                  90                  95

Lys Ile Lys Val Leu Val Ile Glu Lys Gly Phe Tyr Glu Ser Asn Asp
            100                 105                 110

Gly Ala Ile Ile Glu Asp Pro Asn Ala Tyr Gly Gln Ile Phe Gly Thr
        115                 120                 125

Thr Val Asp Gln Asn Tyr Leu Thr Val Pro Leu Ile Asn Asn Arg Thr
    130                 135                 140
```

```
Asn Asn Ile Lys Ala Gly Lys Gly Leu Gly Gly Ser Thr Leu Ile Asn
145                 150                 155                 160

Gly Asp Xaa Trp Thr Arg Pro Asp Lys Ile Gln Ile Asp Ser Trp Glu
            165                 170                 175

Lys Val Phe Gly Met Glu Gly Trp Asn Trp Asp Asn Met Phe Glu Tyr
            180                 185                 190

Met Lys Lys Ala Glu Ala Ala Arg Pro Pro Thr Asp Ala Gln Leu Ala
            195                 200                 205

Ala Gly His Tyr Phe Asp Ala Thr Cys His Gly Thr Asn Gly Thr Val
            210                 215                 220

Arg Ser Gly Ala Arg Asp Asn Gly Lys Pro Trp Ser Pro Leu Met Lys
225                 230                 235                 240

Ala Leu Met Asn Thr Val Ser Ala Leu Gly Val Pro Val Gln Gln Asp
            245                 250                 255

Phe Leu Cys Gly His Pro Arg Gly Val Ser Met Ile Met Asn Asn Val
            260                 265                 270

Asp Glu Asn Gln Val Arg Ala Asp Ala Ala Arg Ala Trp Leu Leu Pro
            275                 280                 285

Asn Tyr Gln Arg Ser Asn Leu Glu Ile Leu Thr Gly Gln Met Val Gly
            290                 295                 300

Lys Val Leu Phe Lys Gln Thr Ala Ser Gly Pro Lys Ala Val Gly Val
305                 310                 315                 320

Asn Phe Gly Thr Asn Lys Val Val Asn Phe Asp Val Phe Ala Lys His
            325                 330                 335

Glu Val Leu Leu Ala Ala Gly Ser Ala Ile Ser Pro Leu Ile Leu Glu
            340                 345                 350

Tyr Ser Gly Ile Gly Leu Lys Ser Val Leu Asp Gln Ala Asn Ile Thr
            355                 360                 365

Gln Leu Leu Asp Leu Pro Val Gly Ile Asn Met Gln Asp Gln Thr Thr
            370                 375                 380

Thr Thr Val Ser Ser Arg Ala Ser Val Ala Gly Ala Gly Gln Gly Gln
385                 390                 395                 400

Ala Val Phe Xaa Ala Asn Phe Thr Glu Thr Phe Gly Asp Tyr Ala Pro
            405                 410                 415

Gln Ala Arg Glu Leu Leu Asn Thr Lys Leu Asp Gln Trp Ala Glu Glu
            420                 425                 430

Thr Val Ala Arg Gly Gly Phe His Asn Val Thr Ala Leu Lys Val Gln
            435                 440                 445

Tyr Glu Asn Tyr Arg Asn Trp Leu Leu Asp Glu Asp Val Ala Phe Ala
450                 455                 460

Glu Leu Phe Met Asp Thr Glu Gly Lys Ile Asn Phe Asp Leu Trp Asp
465                 470                 475                 480

Leu Ile Pro Phe Thr Arg Gly Ser Val His Ile Leu Ser Ser Asp Pro
            485                 490                 495

Tyr Leu Trp Gln Phe Ala Asn Asp Pro Lys Phe Phe Leu Asn Glu Phe
            500                 505                 510

Asp Leu Leu Gly Gln Ala Ala Ser Lys Leu Ala His Asp Leu Ser
            515                 520                 525

Ser Gln Gly Ala Met Lys Glu Tyr Phe Ala Gly Glu Thr Leu Pro Gly
            530                 535                 540

Tyr Asn Leu Ala Glu Asn Ala Thr Leu Ser Gln Trp Ser Ala Tyr Val
545                 550                 555                 560

Leu Gln Asn Phe Arg Pro Asn Trp His Ala Val Ser Ser Cys Ser Met
```

```
                        565                 570                 575

Met Ser Arg Glu Leu Gly Gly Val Val Asp Ala Thr Ala Lys Val Tyr
            580                 585                 590

Gly Thr Gln Gly Leu Arg Val Ile Asp Gly Ser Ile Pro Pro Thr Gln
        595                 600                 605

Val Ser Ser His Val Met Thr Ile Phe Tyr Gly Met Ala Leu Lys Val
    610                 615                 620

Ala Asp Ala Ile Leu Asp Asp Tyr Ala Lys Ser Ala
625                 630                 635

<210> SEQ ID NO 5
<211> LENGTH: 605
<212> TYPE: PRT
<213> ORGANISM: Penicillium variabile
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Ser, then Xaa373 is not Phe

<400> SEQUENCE: 5

Met Val Ser Val Phe Leu Ser Ser Leu Leu Ser Val Ala Thr Ala
1               5                   10                  15

Gln Val Tyr Ser Pro Ala Gln Gln Ile Asp Val Gln Ser Ser Leu Leu
            20                  25                  30

Ser Asp Pro Asn Lys Val Ala Gly Lys Thr Tyr Asp Tyr Ile Ile Ala
        35                  40                  45

Gly Gly Gly Leu Thr Gly Leu Thr Val Ala Ala Lys Leu Ser Glu Asn
    50                  55                  60

Pro Lys Ile Lys Val Leu Val Ile Glu Lys Gly Phe Tyr Glu Ser Asn
65                  70                  75                  80

Asp Gly Ala Ile Ile Glu Asp Ala Asn Ala Tyr Gly Gln Ile Phe Gly
                85                  90                  95

Thr Thr Val Asp Gln Asn Tyr Leu Thr Val Pro Leu Ile Asn Asn Arg
            100                 105                 110

Thr Ser Ser Ile Lys Ser Gly Lys Gly Leu Gly Gly Ser Thr Leu Ile
        115                 120                 125

Asn Gly Asp Xaa Trp Thr Arg Pro Asp Lys Val Gln Ile Asp Ser Trp
    130                 135                 140

Glu Lys Val Phe Gly Met Glu Gly Trp Asn Trp Asp Thr Met Phe Glu
145                 150                 155                 160

Tyr Met Lys Lys Ala Glu Leu Ala Arg Ala Pro Thr Asp Ala Gln Ile
                165                 170                 175

Ala Ala Gly His Tyr Phe Asn Ala Thr Cys His Gly Phe Asn Gly Thr
            180                 185                 190

Ile His Ser Gly Pro Arg Asp Asn Gly Gln Pro Trp Ser Pro Ile Met
        195                 200                 205

Lys Ala Leu Met Asn Thr Thr Ser Ala Leu Gly Ile Pro Thr Gln Gln
    210                 215                 220

Asp Phe Leu Cys Gly His Pro Arg Gly Val Ser Met Ile Tyr Asn Asn
225                 230                 235                 240

Leu Asp Glu Asn Gln Val Arg Ala Asp Ala Gly Arg Ala Trp Val Leu
                245                 250                 255
```

```
Pro Asn Tyr Gln Arg Pro Asn Leu Lys Ile Met Thr Gly Gln Thr Val
            260                 265                 270

Gly Lys Val Leu Phe Asn Gln Thr Ala Ser Gly Pro Lys Ala Val Gly
        275                 280                 285

Val Asn Phe Gly Thr Asn Lys Ala Val Asn Phe Asp Val Tyr Ala Lys
    290                 295                 300

His Glu Val Leu Leu Ala Ala Gly Ser Ala Ile Ser Pro Leu Ile Leu
305                 310                 315                 320

Glu Tyr Ser Gly Ile Gly Leu Lys Ser Val Leu Asp Ala Ala Asn Val
                325                 330                 335

Thr Gln Leu Val Asp Leu Pro Val Gly Leu Asn Met Gln Asp Gln Thr
            340                 345                 350

Thr Thr Thr Val Ser Ser Arg Thr Asn Ala Ala Gly Thr Gly Gln Gly
        355                 360                 365

Gln Ala Val Phe Xaa Ala Asn Phe Thr Glu Val Phe Gly Asp Tyr Thr
    370                 375                 380

Pro Gln Ala Arg Glu Leu Leu Asn Thr Lys Leu Asp Gln Trp Ala Glu
385                 390                 395                 400

Glu Thr Val Ala Arg Gly Gly His Asn Val Thr Ala Leu Lys Ile
                405                 410                 415

Gln Tyr Glu Asn Tyr Arg Asp Trp Leu Leu Glu Glu Asp Val Ala Tyr
            420                 425                 430

Ala Glu Leu Phe Met Asp Thr Ser Gly Lys Ile Asn Phe Asp Leu Trp
        435                 440                 445

Asp Leu Ile Pro Phe Thr Arg Gly Ser Val His Ile Leu Ser Ser Asp
    450                 455                 460

Pro Tyr Leu Trp Gln Tyr Ala Asn Asp Pro Lys Phe Phe Leu Asn Glu
465                 470                 475                 480

Leu Asp Leu Leu Gly Gln Ala Ala Ser Lys Leu Ala Arg Glu Leu
                485                 490                 495

Ser Thr Lys Gly Ala Met Ala Gln Tyr Phe Ala Gly Glu Thr Ile Pro
            500                 505                 510

Gly Asn Asn Leu Ala Ala Asp Ala Asn Leu Ser Gln Trp Ser Asp Tyr
        515                 520                 525

Val Ile Gln Asn Phe Arg Pro Asn Trp His Ala Val Ser Ser Cys Ser
    530                 535                 540

Met Met Ala Lys Glu Leu Gly Gly Val Val Asp Ala Thr Ala Lys Val
545                 550                 555                 560

Tyr Gly Thr Gln Gly Leu Arg Val Val Asp Gly Ser Ile Pro Pro Thr
                565                 570                 575

Gln Val Ser Ser His Val Met Thr Ile Phe Tyr Gly Met Ala Leu Lys
            580                 585                 590

Val Ala Asp Ala Ile Leu Ala Asp Tyr Ala Lys Ser Ala
        595                 600                 605

<210> SEQ ID NO 6
<211> LENGTH: 604
<212> TYPE: PRT
<213> ORGANISM: Penicillium chrysogenum
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
```

<222> LOCATION: (372)..(372)
<223> OTHER INFORMATION: Xaa is Phe, Ala, Leu, Trp or Tyr, provided that
      when Xaa132 is Ser, then Xaa372 is not Phe

<400> SEQUENCE: 6

```
Met Lys Ser Thr Ile Ile Thr Ser Ile Leu Phe Ser Val Ala Ala Val
1               5                   10                  15

Gln Ala Tyr Ser Pro Ala Glu Gln Ile Asp Val Gln Ser His Leu Leu
            20                  25                  30

Ser Asp Pro Thr Lys Val Glu Gly Glu Thr Tyr Asp Tyr Val Ile Ala
        35                  40                  45

Gly Gly Gly Leu Thr Gly Leu Thr Val Ala Ala Lys Leu Ser Glu Asn
50                  55                  60

Pro Lys Ile Lys Val Leu Val Ile Glu Lys Gly Phe Tyr Glu Ser Asn
65                  70                  75                  80

Asp Gly Pro Ile Ile Glu Asp Pro Asn Ala Tyr Gly Glu Ile Phe Gly
                85                  90                  95

Thr Ser Val Asp Gln Asn Tyr Leu Thr Val Pro Leu Ile Asn Asn Arg
            100                 105                 110

Thr Gly Glu Ile Lys Ser Gly Leu Gly Leu Gly Gly Ser Thr Leu Ile
        115                 120                 125

Asn Gly Asp Xaa Trp Thr Arg Pro Asp Lys Val Gln Ile Asp Ser Trp
    130                 135                 140

Glu Lys Val Phe Gly Met Glu Gly Trp Asn Trp Asp Asn Val Phe Gln
145                 150                 155                 160

Tyr Met Gln Lys Ala Glu Arg Ser Arg Pro Pro Thr Ala Ala Gln Ile
                165                 170                 175

Glu Ala Gly His Phe Tyr Asp Pro Ala Cys His Gly Thr Asp Gly Thr
            180                 185                 190

Val His Ala Gly Pro Arg Asp Asn Gly Lys Pro Trp Ser Pro Leu Met
        195                 200                 205

Arg Ala Leu Met Asn Thr Val Ser Ala Phe Gly Val Pro Val Gln Lys
210                 215                 220

Asp Phe His Cys Gly His Pro Arg Gly Val Ser Met Ile Pro Asn Asn
225                 230                 235                 240

Leu His Glu Asn Gln Ile Arg Ala Asp Ala Ala Arg Glu Trp Leu Leu
                245                 250                 255

Pro Asn Tyr Gln Arg Asp Asn Leu Gln Ile Leu Thr Gly Gln Lys Val
            260                 265                 270

Gly Lys Val Leu Phe Asn Gln Thr Ala Ser Gly Pro Lys Ala Val Gly
        275                 280                 285

Val Asn Phe Gly Thr Asn Lys Ala Val Asn Phe Asn Val Tyr Ala Lys
290                 295                 300

Gln Glu Val Leu Leu Ala Ala Gly Ser Ala Ile Ser Pro Leu Ile Leu
305                 310                 315                 320

Glu Tyr Ser Gly Ile Gly Ile Lys Ser Val Leu Asp Lys Ala Gly Val
                325                 330                 335

Lys Gln Leu Leu Glu Leu Pro Val Gly Leu Asn Met Gln Asp Gln Thr
            340                 345                 350

Thr Thr Thr Val Arg Ser Arg Ala Asn Asn Ala Pro Gly Gln Gly Gln
        355                 360                 365

Ala Ala Tyr Xaa Ala Asn Phe Thr Glu Val Leu Gly Asp His Ala Ala
370                 375                 380

Gln Gly Ile Lys Leu Leu Asp Thr Lys Leu Asp Gln Trp Ala Glu Glu
```

```
                385                 390                 395                 400
    Thr Val Ala Arg Gly Gly Phe His Asn Val Thr Ala Leu Lys Ile Gln
                    405                 410                 415

Tyr Glu Asn Tyr Arg Asn Trp Leu Leu Asp Glu Asp Val Ala Phe Ala
                420                 425                 430

Glu Leu Phe Phe Asp Thr Glu Gly Lys Ile Asn Phe Asp Ile Trp Asn
                    435                 440                 445

Leu Ile Pro Phe Thr Arg Gly Ser Val His Ile Leu Ser Ser Asp Pro
    450                 455                 460

Tyr Leu Trp Gln Tyr Ala Asn Asp Pro Lys Phe Phe Met Asn Glu Leu
    465                 470                 475                 480

Asp Leu Leu Gly Gln Ala Ala Ala Thr Lys Leu Gly Arg Glu Leu Ser
                    485                 490                 495

Ser Ala Gly Glu Met Lys Lys Tyr Tyr Ala Gly Glu Thr Ile Pro Gly
                500                 505                 510

Asp Asn Leu Pro Gln Asp Ala Thr Val Glu Gln Trp Glu Asp Tyr Val
                    515                 520                 525

Met Met Asn Phe Arg Pro Asn Trp His Ala Val Ser Thr Cys Ser Met
    530                 535                 540

Met Ser Arg Glu Leu Gly Gly Val Val Asp Ala Thr Ala Lys Val Tyr
    545                 550                 555                 560

Gly Thr Gln Gly Leu Arg Val Ile Asp Gly Ser Ile Pro Pro Thr Gln
                    565                 570                 575

Val Ser Ser His Val Met Thr Val Phe Tyr Gly Met Ala Leu Arg Ile
                580                 585                 590

Ala Glu Ser Val Leu Glu Asp Tyr Ala Lys Lys Ala
                    595                 600

<210> SEQ ID NO 7
<211> LENGTH: 628
<212> TYPE: PRT
<213> ORGANISM: Aspergillus terreus
<220> FEATURE:
<221> NAME/KEY: MISC_FEATURE
<222> LOCATION: (156)..(156)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (397)..(397)
<223> OTHER INFORMATION: Xaa is Phe, Ala, Leu, Trp or Tyr, provided that
      when Xaa156 is Ser, then Xaa397 is not Phe

<400> SEQUENCE: 7

Met Leu Gln Leu Ser Leu Thr Ala Phe Arg Ser Phe His Phe His Thr
1               5                   10                  15

Gly Pro His Pro Leu Lys Thr Thr Ile Ala Met Arg His Ile Ser Tyr
                20                  25                  30

Phe Leu Leu Pro Leu Ala Thr Val Ser Ala Tyr Leu Val Ser Glu Gln
            35                  40                  45

Val Asn Val Gln Ala Ser Leu Leu Thr Asn Pro Glu Asp Val Ala Asp
        50                  55                  60

Lys Lys Phe Asp Tyr Ile Ile Ala Gly Gly Leu Thr Gly Leu Thr
65                  70                  75                  80

Val Ala Ala Lys Leu Thr Glu Asn Pro Asn Ile Glu Val Leu Val Ile
                85                  90                  95

Glu Lys Gly Phe Tyr Glu Ser Asn Asp Gly Thr Ile Ile Glu Asp Pro
            100                 105                 110
```

```
Asn Ala Tyr Gly Gln Ile Phe Gly Thr Thr Val Asp Gln Asn Tyr Leu
            115                 120                 125
Thr Val Pro Leu Ile Asn Asn Arg Thr Asp Asn Ile Lys Ser Gly Lys
        130                 135                 140
Gly Leu Gly Gly Ser Thr Leu Ile Asn Gly Asp Xaa Trp Thr Arg Pro
145                 150                 155                 160
Asp Lys Val Gln Ile Asp Ser Trp Glu Lys Val Phe Gly Asn Glu Gly
                165                 170                 175
Trp Asn Trp Asp Asn Val Phe Lys Tyr Met Asn Gln Ala Glu Arg Ala
            180                 185                 190
Arg Ala Pro Asn Ala Ala Gln Val Ala Ala Gly His His Phe Asp Pro
        195                 200                 205
Thr Cys His Gly Phe Asn Gly Thr Val His Ala Gly Pro Arg Asp Asn
    210                 215                 220
Gly Gln Pro Trp Ser Pro Leu Met Lys Ala Leu Met Asn Thr Thr Ser
225                 230                 235                 240
Ala Leu Gly Val Pro Thr Gln Val Asp Phe His Cys Gly His Pro Arg
                245                 250                 255
Gly Val Ser Met Ile Pro Asn Asn Leu Leu Glu Asp Gln Val Arg Ala
            260                 265                 270
Asp Ala Ala Arg Glu Trp Leu Leu Pro Asn Tyr Arg Arg Lys Asn Leu
        275                 280                 285
Lys Val Leu Thr Gly Gln Val Val Gly Lys Val Ile Phe Asp Gln Asp
    290                 295                 300
Ala Pro Ser Leu Lys Ala Ile Gly Val Asn Phe Gly Thr Asn Lys Ala
305                 310                 315                 320
Val Asn Phe Asn Val Tyr Ala Asn His Glu Val Leu Leu Ala Ala Gly
                325                 330                 335
Ser Ala Ile Ser Pro Leu Ile Leu Glu Tyr Ser Gly Ile Gly Leu Lys
            340                 345                 350
Ser Val Leu Asp Lys Ala Asn Val Pro Gln Leu Leu Glu Leu Pro Val
        355                 360                 365
Gly Ile Asn Met Gln Asp Gln Thr Thr Thr Val Arg Ala Arg Ser
    370                 375                 380
Thr Pro Ala Gly Phe Gly Gln Gly Gln Ala Val Tyr Xaa Ala Asn Phe
385                 390                 395                 400
Thr Glu Thr Phe Gly Glu Asp Ala Pro Tyr Ala Ala Glu Leu Leu Asn
                405                 410                 415
Thr Lys Leu Asp Gln Trp Ala Glu Glu Thr Val Ala Arg Gly Gly Ser
            420                 425                 430
His Asn Val Thr Ala Leu Lys Val Gln Tyr Glu Asn Tyr Arg Asp Trp
        435                 440                 445
Leu Leu Asn Glu Asp Val Ala Tyr Ala Glu Leu Phe Leu Asp Thr Ser
    450                 455                 460
Gly Gln Ile Asn Phe Asp Leu Trp Asp Leu Ile Pro Phe Thr Arg Gly
465                 470                 475                 480
Ser Thr His Ile Leu Ser Ser Asp Pro Tyr Leu Trp Gln Phe Ala Asn
                485                 490                 495
Asp Pro Lys Phe Phe Phe Asn Glu Leu Asp Leu Leu Gly Gln Ala Ala
            500                 505                 510
Ala Ser Arg Leu Ala Arg Thr Leu Gln Asn Ser Gly Ala Met Ala Asn
        515                 520                 525
```

```
Tyr Phe Asn Gly Glu Ile Ile Pro Gly Ser Glu Leu Pro Tyr Glu Ala
            530                 535                 540

Ser Leu Glu Gln Trp Ala Glu Tyr Val Lys Asp Asn Phe Arg Ala Asn
545                 550                 555                 560

Trp His Ala Val Gly Thr Cys Ser Met Met Ser Arg Asp Leu Gly Gly
                565                 570                 575

Val Val Asp Ala Thr Ala Lys Val Tyr Asp Thr Gln Gly Leu Arg Val
            580                 585                 590

Ile Asp Gly Ser Ile Pro Pro Thr Gln Val Ser Ser His Val Met Thr
        595                 600                 605

Ile Phe Tyr Gly Met Ala Leu Arg Ile Ala Glu Ser Ile Leu Glu Asp
610                 615                 620

Tyr Ala Lys Ala
625

<210> SEQ ID NO 8
<211> LENGTH: 602
<212> TYPE: PRT
<213> ORGANISM: Aspergillus terreus
<220> FEATURE:
<221> NAME/KEY: MISC_FEATURE
<222> LOCATION: (130)..(130)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (371)..(371)
<223> OTHER INFORMATION: Xaa is Phe, Ala, Leu, Trp or Tyr, provided that
      when Xaa130 is Ser, then Xaa371 is not Phe

<400> SEQUENCE: 8

Met Arg His Ile Gly Tyr Phe Leu Leu Pro Leu Ala Thr Val Cys Ala
1               5                   10                  15

Tyr Leu Val Ser Glu Gln Val Asp Val Gln Ala Ser Leu Leu Thr Asn
            20                  25                  30

Pro Glu Glu Val Ala Asp Lys Asn Phe Asp Tyr Ile Ile Ala Gly Gly
        35                  40                  45

Gly Leu Thr Gly Leu Thr Val Ala Ala Lys Leu Thr Glu Asn Pro Asn
50                  55                  60

Ile Glu Val Leu Val Ile Glu Lys Gly Phe Tyr Glu Ser Asn Asp Gly
65                  70                  75                  80

Pro Ile Ile Glu Asp Pro Asn Ala Tyr Gly Gln Ile Phe Gly Thr Thr
                85                  90                  95

Val Asp Gln Asn Tyr Leu Thr Val Pro Leu Ile Asn Asn Arg Thr Asp
            100                 105                 110

Asn Ile Lys Ser Gly Lys Gly Leu Gly Gly Ser Thr Leu Ile Asn Gly
        115                 120                 125

Asp Xaa Trp Thr Arg Pro Asp Lys Val Gln Ile Asp Ser Trp Glu Thr
130                 135                 140

Val Phe Gly Asn Glu Gly Trp Asn Trp Asp Asn Val Phe Lys Tyr Met
145                 150                 155                 160

Asn Gln Ala Glu Arg Ala Arg Ala Pro Asn Ala Thr Gln Ile Ala Ala
                165                 170                 175

Gly His His Phe Asp Pro Ala Cys His Gly Phe Asn Gly Thr Val His
            180                 185                 190

Ala Gly Pro Arg Asp Asn Gly Gln Arg Trp Ser Pro Leu Met Lys Ala
        195                 200                 205

Leu Met Asn Thr Thr Ser Ala Leu Gly Val Pro Thr Gln Val Asp Phe
```

```
                 210                 215                 220

His Cys Gly His Pro Arg Gly Val Ser Met Ile Pro Asn Asn Leu Leu
225                 230                 235                 240

Glu Asp Gln Val Arg Ala Asp Ala His Glu Trp Leu Leu Pro Asn
            245                 250                 255

Tyr Arg Arg Lys Asn Leu Lys Val Leu Thr Gly Gln Leu Val Gly Lys
                260                 265                 270

Val Ile Phe Asp Gln Asp Ala Pro Gly Leu Lys Ala Ile Gly Val Asn
            275                 280                 285

Phe Gly Thr Asn Lys Ala Val Asn Phe Asn Val Tyr Ala Asn His Glu
290                 295                 300

Val Leu Leu Ala Ala Gly Ser Ala Ile Ser Pro Leu Ile Leu Glu Tyr
305                 310                 315                 320

Ser Gly Ile Gly Leu Arg Ser Val Leu Glu Lys Ala Asn Val Pro Gln
                325                 330                 335

Leu Leu Glu Leu Pro Val Gly Ile Asn Met Gln Asp Gln Thr Thr Thr
            340                 345                 350

Thr Val Arg Ala Arg Ser Thr Pro Ala Gly Phe Gly Gln Gly Gln Ala
            355                 360                 365

Val Tyr Xaa Ala Asn Phe Thr Glu Thr Phe Glu Asp Ala Pro Tyr
370                 375                 380

Ala Ala Glu Leu Leu Lys Thr Gln Leu Asp Gln Trp Ala Glu Glu Thr
385                 390                 395                 400

Val Ala Arg Gly Gly Phe His Asn Val Thr Ala Leu Lys Val Gln Tyr
            405                 410                 415

Glu Asn Tyr Arg Asp Trp Leu Leu Asn Glu Asp Val Ala Tyr Ala Glu
            420                 425                 430

Leu Phe Leu Asp Thr Ser Gly Gln Ile Asn Phe Asp Leu Trp Asp Leu
            435                 440                 445

Ile Pro Phe Thr Arg Gly Ser Thr His Ile Leu Ser Ser Asp Pro Tyr
            450                 455                 460

Leu Trp Gln Phe Ala Asn Asp Pro Lys Phe Phe Asn Glu Leu Asp
465                 470                 475                 480

Leu Leu Gly Gln Ala Ala Ser Arg Leu Ala Arg Lys Leu Gln Asn
                485                 490                 495

Ser Gly Ala Met Ala Asn Tyr Phe Asp Gly Glu Ile Ile Pro Gly Ser
            500                 505                 510

Glu Leu Pro Asn Glu Ala Ser Leu Glu Gln Trp Ala Glu Tyr Val Lys
            515                 520                 525

Asp Asn Phe Arg Ala Asn Trp His Ala Val Gly Thr Cys Ser Met Met
530                 535                 540

Ser Lys Asp Leu Gly Gly Val Val Asp Ala Ser Ala Lys Val Tyr Asp
545                 550                 555                 560

Thr Gln Arg Leu Arg Val Ile Asp Gly Ser Ile Pro Pro Thr Gln Val
                565                 570                 575

Ser Ser His Val Met Thr Ile Phe Tyr Gly Met Ala Leu Arg Ile Ala
            580                 585                 590

Glu Ser Ile Leu Glu Asp Tyr Ala Lys Ala
            595                 600

<210> SEQ ID NO 9
<211> LENGTH: 605
<212> TYPE: PRT
<213> ORGANISM: Aspergillus oryzae
```

<220> FEATURE:
<221> NAME/KEY: MISC_FEATURE
<222> LOCATION: (133)..(133)
<223> OTHER INFORMATION: Xaa is Ser, Ala, Cys, Ile, Asn, Arg, Asp, Thr, Val, Tyr, Glu, His, Met or Gln
<220> FEATURE:
<221> NAME/KEY: MISC_FEATURE
<222> LOCATION: (374)..(374)
<223> OTHER INFORMATION: Xaa is Phe, Ala, Leu, Trp or Tyr, provided that when Xaa133 is Ser, then Xaa374 is not Phe

<400> SEQUENCE: 9

```
Met Lys Ser Ala Ile Phe Ser Pro Ile Leu Phe Ser Leu Ala Leu Ala
1               5                   10                  15

Gln Asn Tyr Ser Leu Glu Lys His Phe Asp Val Gln Ser Ser Leu Ile
            20                  25                  30

Ser Asp Pro Lys Glu Val Ser Glu Lys Thr Phe Asp Tyr Val Ile Ala
        35                  40                  45

Gly Gly Gly Leu Thr Gly Leu Thr Val Ala Thr Lys Leu Thr Glu Asn
    50                  55                  60

Pro Asp Ile Glu Val Leu Val Ile Glu Lys Gly Phe Tyr Glu Ser Asn
65                  70                  75                  80

Cys Gly Ser Ile Val Glu Asp Leu Asn Glu Tyr Gly Asp Ile Phe Gly
                85                  90                  95

Thr Asp Val Asp Gln Ala Tyr Gln Thr Val Pro Leu Ala Val Asn Asn
            100                 105                 110

Arg Thr Glu Leu Ile Arg Ser Gly Asn Gly Leu Gly Gly Ser Thr Leu
        115                 120                 125

Ile Asn Gly Gly Xaa Trp Thr Arg Pro Asp Lys Val Gln Ile Asp Ser
    130                 135                 140

Trp Glu Arg Val Phe Gly Asn Glu Gly Trp Asn Trp Asp Ser Leu Phe
145                 150                 155                 160

Glu Tyr Met Lys Lys Ala Glu His Ser Arg Pro Pro Asn Glu Ala Gln
                165                 170                 175

Ile Ala Ala Gly His Ser Tyr Asp Pro Ala Cys His Gly Thr Asn Gly
            180                 185                 190

Thr Val Gln Ala Gly Pro Arg Asp Asn Gly Lys Pro Trp Ser Pro Ile
        195                 200                 205

Met Lys Ala Leu Ile Asn Thr Ala Ser Glu Arg Gly Val Pro Thr Gln
    210                 215                 220

Gln Asp Phe His Cys Gly His Pro Arg Gly Val Ser Met Ile Pro Asn
225                 230                 235                 240

Ala Val His Glu Asp Gln Thr Arg Ser Asp Thr Ala Arg Glu Trp Leu
                245                 250                 255

Leu Pro Asn His Glu Arg Pro Asn Leu Lys Val Leu Thr Gly Gln Arg
            260                 265                 270

Val Gly Lys Val Leu Leu Asn Lys Thr Glu Ser Gly Ala Lys Ala Thr
        275                 280                 285

Gly Leu Asn Phe Gly Thr His Arg Lys Val Asn Tyr Asn Val Tyr Ala
    290                 295                 300

Lys His Glu Val Leu Leu Ala Ala Gly Ser Ala Ile Ser Pro Leu Ile
305                 310                 315                 320

Leu Glu Trp Ser Gly Ile Gly Leu Lys Asp Val Leu Ser Ala Ala Gly
                325                 330                 335

Val Glu Val Val Asp Leu Pro Val Gly Leu Asn Met Gln Asp Gln
            340                 345                 350
```

```
Thr Thr Thr Asn Val Arg Ser Gln Ala Gln Ala Ser Gly Ala Gly Gln
        355                 360                 365

Gly Gln Ala Val Tyr Xaa Ala Ser Phe Asn Glu Thr Phe Gly Asp Tyr
    370                 375                 380

Ala His Lys Ala Met Glu Leu Leu Asn Thr Lys Leu Asp Gln Trp Ala
385                 390                 395                 400

Glu Glu Thr Val Arg Asn Gly Gly Phe His Asn Val Thr Ala Leu Lys
                405                 410                 415

Ile Gln Tyr Glu Asn Tyr Arg Asp Trp Leu Leu Asn Glu Asp Val Ala
            420                 425                 430

Phe Ala Glu Leu Phe Leu Asp Thr Glu Gly Lys Ile Asn Phe Asp Leu
        435                 440                 445

Trp Asp Leu Ile Pro Phe Thr Arg Gly Ser Val His Ile Leu Asn Gly
    450                 455                 460

Asp Pro Tyr Leu His Arg Tyr Ala Asn Asp Pro Lys Phe Phe Leu Asn
465                 470                 475                 480

Glu Phe Asp Ile Leu Gly Gln Ala Ala Thr Lys Leu Ala Arg Glu
                485                 490                 495

Leu Ser Asn Thr Gly Glu Met Lys Lys Tyr Phe Ala Gly Glu Ile Ile
            500                 505                 510

Pro Gly Asp Asn Leu Ala Tyr Asp Ala Ser Leu Glu Gln Trp Ala Asp
        515                 520                 525

Tyr Val Lys Glu Asn Phe Arg Ala Asn Trp His Ala Val Ser Ser Cys
    530                 535                 540

Ser Met Met Ser Arg Glu Met Gly Gly Val Val Asp Ser Ala Ala Arg
545                 550                 555                 560

Val Tyr Asp Val Glu Asn Leu Arg Ile Val Asp Gly Ser Ile Pro Pro
                565                 570                 575

Thr Gln Val Ser Ser His Val Met Thr Ile Phe Tyr Gly Met Ala Leu
            580                 585                 590

Lys Val Ala Asp Ala Ile Leu Ala Asp Tyr Ser Lys Asn
        595                 600                 605

<210> SEQ ID NO 10
<211> LENGTH: 605
<212> TYPE: PRT
<213> ORGANISM: Aspergillus flavus
<220> FEATURE:
<221> NAME/KEY: MISC_FEATURE
<222> LOCATION: (133)..(133)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (374)..(374)
<223> OTHER INFORMATION: Xaa is Phe, Ala, Leu, Trp or Tyr, provided that
      when Xaa133 is Ser, then Xaa374 is not Phe

<400> SEQUENCE: 10

Met Lys Ser Ala Ile Phe Ser Pro Ile Leu Phe Ser Leu Ala Leu Ala
1               5                   10                  15

Gln Asn Tyr Ser Leu Glu Lys His Phe Asp Val Gln Ser Ser Leu Ile
            20                  25                  30

Ser Asp Pro Lys Glu Val Ser Glu Lys Thr Phe Asp Tyr Val Ile Ala
        35                  40                  45

Gly Gly Gly Leu Thr Gly Leu Thr Val Ala Thr Lys Leu Thr Glu Asn
    50                  55                  60

Pro Asp Ile Glu Val Leu Val Ile Glu Lys Gly Phe Tyr Glu Ser Asn
```

```
                     65                  70                  75                  80
Cys Gly Ser Ile Val Glu Asp Leu Asn Glu Tyr Gly Asp Ile Phe Gly
                         85                  90                  95
Thr Asp Val Asp Gln Ala Tyr Gln Thr Val Pro Leu Ala Val Asn Asn
                    100                 105                 110
Arg Thr Glu Leu Ile Arg Ser Gly Asn Gly Leu Gly Ser Thr Leu
                115                 120                 125
Ile Asn Gly Gly Xaa Trp Thr Arg Pro Asp Lys Val Gln Ile Asp Ser
    130                 135                 140
Trp Glu Arg Val Phe Gly Asn Glu Gly Trp Asn Trp Asp Ser Leu Phe
145                 150                 155                 160
Glu Tyr Met Lys Lys Ala Glu His Ser Arg Pro Pro Asn Glu Ala Gln
                165                 170                 175
Ile Ala Ala Gly His Ser Tyr Asp Pro Ala Cys His Gly Thr Asn Gly
            180                 185                 190
Thr Val Gln Ala Gly Pro Arg Asp Asn Gly Lys Pro Trp Ser Pro Ile
                195                 200                 205
Ile Lys Ala Leu Ile Asn Thr Ala Ser Glu Arg Gly Val Pro Thr Gln
    210                 215                 220
Gln Asp Phe His Cys Gly His Pro Arg Gly Val Ser Met Ile Pro Asn
225                 230                 235                 240
Ala Val His Glu Asp Gln Thr Arg Ser Asp Thr Ala Arg Glu Trp Leu
                245                 250                 255
Leu Pro Asn His Glu Arg Pro Asn Leu Lys Val Leu Thr Gly Gln Arg
                260                 265                 270
Val Gly Lys Val Leu Leu Asn Lys Thr Glu Ser Gly Ala Lys Ala Thr
            275                 280                 285
Gly Leu Asn Phe Gly Thr His Arg Lys Val Asn Tyr Asn Val Tyr Ala
    290                 295                 300
Lys His Glu Val Leu Leu Ala Ala Gly Ser Ala Ile Ser Pro Leu Ile
305                 310                 315                 320
Leu Glu Trp Ser Gly Ile Gly Leu Lys Asp Val Leu Ser Ala Ala Gly
                325                 330                 335
Val Glu Gln Val Val Asp Leu Pro Val Gly Leu Asn Met Gln Asp Gln
                340                 345                 350
Thr Thr Thr Asn Val Arg Ser Gln Ala Gln Ala Ser Gly Ala Gly Gln
            355                 360                 365
Gly Gln Ala Val Tyr Xaa Ala Ser Phe Asn Glu Thr Phe Gly Asp Tyr
    370                 375                 380
Ala His Lys Ala Met Glu Leu Leu Asn Thr Lys Leu Asp Gln Trp Ala
385                 390                 395                 400
Glu Glu Thr Val Arg Asn Gly Gly Phe His Asn Val Thr Ala Leu Lys
                405                 410                 415
Ile Gln Tyr Glu Asn Tyr Arg Asp Trp Leu Leu Asn Glu Asp Val Ala
                420                 425                 430
Phe Ala Glu Leu Phe Leu Asp Thr Glu Gly Lys Ile Asn Phe Asp Leu
            435                 440                 445
Trp Asp Leu Ile Pro Phe Thr Arg Gly Ser Val His Ile Leu Asn Gly
    450                 455                 460
Asp Pro Tyr Leu His Arg Tyr Ala Asn Asp Pro Lys Phe Phe Leu Asn
465                 470                 475                 480
Glu Phe Asp Ile Leu Gly Gln Ala Ala Thr Lys Leu Ala Arg Glu
                485                 490                 495
```

```
Leu Ser Asn Thr Gly Glu Met Lys Lys Tyr Phe Ala Gly Glu Ile Ile
            500                 505                 510

Pro Gly Asp Asn Leu Ala Tyr Asp Ala Ser Leu Glu Gln Trp Ala Asp
            515                 520                 525

Tyr Val Lys Glu Asn Phe Arg Ala Asn Trp His Ala Val Ser Ser Cys
            530                 535                 540

Ser Met Met Ser Arg Glu Met Gly Gly Val Val Asp Ser Ala Ala Arg
545                 550                 555                 560

Val Tyr Asp Val Glu Asn Leu Arg Ile Val Asp Gly Ser Ile Pro Pro
                565                 570                 575

Thr Gln Val Ser Ser His Val Met Thr Ile Phe Tyr Gly Met Ala Leu
            580                 585                 590

Lys Val Ala Asp Ala Ile Leu Ala Asp Tyr Ser Lys Asn
            595                 600                 605

<210> SEQ ID NO 11
<211> LENGTH: 606
<212> TYPE: PRT
<213> ORGANISM: Aspergillus terreus
<220> FEATURE:
<221> NAME/KEY: MISC_FEATURE
<222> LOCATION: (133)..(133)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (374)..(374)
<223> OTHER INFORMATION: Xaa is Phe, Ala, Leu, Trp or Tyr, provided that
      when Xaa133 is Ser, then Xaa374 is not Phe

<400> SEQUENCE: 11

Met Lys Gly Thr Phe Leu Val Ser Ala Leu Ala Phe Thr Ala Ile Thr
1               5                   10                  15

Gln Ala Phe Thr Pro Ala Glu Gln Ile Asp Val Gln Ser Ser Leu Ile
            20                  25                  30

Ser Asp Pro Lys Glu Val Ala Gly Lys Glu Val Asp Tyr Ile Ile Ala
        35                  40                  45

Gly Gly Gly Leu Thr Gly Leu Thr Val Ala Ala Lys Leu Thr Glu Asp
    50                  55                  60

Pro Asp Ile Arg Val Leu Val Ile Glu Lys Gly Phe Tyr Glu Ser Asn
65                  70                  75                  80

Asn Gly Pro Ile Ile Glu Asp Leu Asn Ala Tyr Gly Asp Ile Phe Gly
                85                  90                  95

Ser Thr Val Asp Gln Asn Tyr Leu Thr Val Pro Met Gly Ile Asn Asn
            100                 105                 110

Arg Thr Leu Asp Ile Lys Ser Gly Lys Gly Leu Gly Gly Ser Thr Leu
        115                 120                 125

Val Asn Gly Gly Xaa Trp Thr Ser Pro Asp Lys Val Gln Leu Asp Ser
    130                 135                 140

Trp Glu Thr Val Leu Gly Asn Pro Gly Trp Asn Trp Glu Thr Ile Phe
145                 150                 155                 160

Glu Tyr Lys Lys Lys Ala Glu Arg Ala Arg Tyr Pro Thr Ala Glu Glu
                165                 170                 175

Ile Met Ala Gly Gln His Ile Asp Ala Ala Cys His Gly Phe Asn Gly
            180                 185                 190

Thr Val His Ala Gly Val Arg Asn Thr Gly Glu Pro Tyr Ser Pro Met
        195                 200                 205
```

```
Ile Arg Ala Leu Met Asn Thr Thr Glu Ala Met Gly Ile Pro Thr Gln
            210                 215                 220

Val Asp Leu His Cys Gly His Pro Arg Gly Val Ser Met Ile Leu Asn
225                 230                 235                 240

Ser Leu His Glu Asp Gln Thr Arg Ser Asp Ala Ala Arg Glu Trp Leu
            245                 250                 255

Leu Pro Asn Tyr Glu Arg Pro Asn Leu Gln Val Leu Thr Gly Gln Ile
            260                 265                 270

Val Gly Lys Val Leu Phe Glu Ser Thr Gly Asn Gly Pro Lys Ala Val
            275                 280                 285

Gly Val Asn Tyr Gly Thr Asn Lys Asp Val Asn Phe Asn Val Tyr Ala
            290                 295                 300

Lys His Glu Val Leu Leu Ala Ala Gly Ser Ala Val Ser Pro Leu Ile
305                 310                 315                 320

Leu Glu His Ser Gly Ile Gly Leu Lys Ser Val Leu Gly Pro Leu Gly
            325                 330                 335

Ile Ala Gln Leu Val Glu Leu Pro Val Gly Leu Asn Met Gln Asp Gln
            340                 345                 350

Thr Thr Thr Thr Val Gln Ser Arg Ala Lys Gly Thr Gly Ala Gly Gln
            355                 360                 365

Gly Gln Ala Val Tyr Xaa Ala Asn Phe Thr Glu Thr Phe Gly Asp His
            370                 375                 380

Ala Pro His Ala Met Lys Leu Leu Asn Thr Lys Leu Asp Gln Trp Ala
385                 390                 395                 400

Thr Glu Thr Val Ala Arg Gly Gly Phe His Asn Val Thr Ala Leu Lys
            405                 410                 415

Val Gln Tyr Glu Asn Tyr Arg Lys Trp Leu Leu Glu Asp Asp Val Ala
            420                 425                 430

Phe Val Glu Phe Phe Phe Asp Ser Asn Gly Met Ile Asn Phe Asp Leu
            435                 440                 445

Trp Asp Leu Ile Pro Phe Thr Arg Gly Ser Thr His Ile Ala Asp Pro
            450                 455                 460

Asp Pro Tyr Leu Gln Ser Phe Leu Asn Asn Pro Met Phe Phe Leu Asn
465                 470                 475                 480

Glu Phe Asp Leu Leu Gly Gln Ala Ala Ala Ser Lys Leu Ala Arg Glu
            485                 490                 495

Leu Gln Asn Met Gly Glu Met Arg Asp Tyr Phe Ala Gly Glu Asn Ile
            500                 505                 510

Pro Gly Ala Glu Leu Leu Ala Tyr Asp Ala Ser Leu Glu Glu Trp Val
            515                 520                 525

Glu Tyr Val Lys Gln Asn Phe Arg Ala Asn Trp His Ala Val Ser Thr
            530                 535                 540

Cys Ala Met Met Ser Lys Glu Leu Gly Gly Val Val Asp Pro Thr Ala
545                 550                 555                 560

Lys Val Tyr Gly Thr Gln Gly Leu Arg Val Ile Asp Gly Ser Ile Val
            565                 570                 575

Pro Thr Gln Ile Ser Ala His Val Met Thr Thr Phe Tyr Ala Met Ala
            580                 585                 590

Leu Lys Ile Ser Asp Ser Ile Leu Glu Asp Tyr Tyr Arg His
            595                 600                 605

<210> SEQ ID NO 12
<211> LENGTH: 583
<212> TYPE: PRT
```

```
<213> ORGANISM: Aspergillus niger
<220> FEATURE:
<221> NAME/KEY: MISC_FEATURE
<222> LOCATION: (110)..(110)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (351)..(351)
<223> OTHER INFORMATION: Xaa is Phe, Ala, Leu, Trp or Tyr, provided that
      when Xaa110 is Thr, then Xaa351 is not Phe

<400> SEQUENCE: 12

Ser Asn Gly Ile Glu Ala Ser Leu Leu Thr Asp Pro Asn Asp Val Ser
1               5                   10                  15

Gly Arg Thr Val Asp Tyr Ile Ile Ala Gly Gly Leu Thr Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Xaa Trp Thr
                100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Thr Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Gln Lys Asp Phe Gly Cys Gly Asp
                195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Xaa Ala
            340                 345                 350
```

```
Thr Phe Asn Glu Thr Phe Gly Asp Tyr Ser Glu Lys Ala His Glu Leu
            355                 360                 365

Leu Asn Thr Lys Leu Glu Gln Trp Ala Glu Ala Val Ala Arg Gly
        370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
        450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 13
<211> LENGTH: 605
<212> TYPE: PRT
<213> ORGANISM: Aspergillus niger
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Thr, then Xaa373 is not Phe

<400> SEQUENCE: 13

Met Gln Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80
```

```
Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
            115                 120                 125

Asn Gly Gly Xaa Trp Thr Arg Pro His Lys Ala Gln Val Asp Ser Trp
        130                 135                 140

Glu Thr Val Phe Gly Asn Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
            195                 200                 205

Lys Ala Leu Met Ser Ala Val Glu Asp Arg Gly Val Pro Thr Lys Lys
        210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Gln Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365

Gln Ala Ala Trp Xaa Ala Thr Phe Asn Glu Thr Phe Gly Asp Tyr Ala
        370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
    450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
```

```
                500                 505                 510
Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Ile Ala Asp Ala Ile Leu Ala Asp Tyr Ala Ser Met Gln
        595                 600                 605

<210> SEQ ID NO 14
<211> LENGTH: 605
<212> TYPE: PRT
<213> ORGANISM: Apergillus niger
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Thr, then Xaa373 is not Phe

<400> SEQUENCE: 14

Met Gln Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Asp Val Ser Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asn Ile Ser Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Xaa Trp Thr Arg Pro His Lys Ala Gln Val Asp Ser Trp
    130                 135                 140

Glu Thr Val Phe Gly Asn Glu Gly Trp Asn Trp Asp Asn Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Val Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220
```

```
Asp Phe Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
            245                 250                 255

Pro Asn Tyr Gln Arg Pro Asn Leu Gln Val Leu Thr Gly Gln Tyr Val
        260                 265                 270

Gly Lys Val Leu Leu Ser Gln Asn Gly Thr Thr Pro Arg Ala Val Gly
    275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ala Thr Val Arg Ser Arg Ile Thr Ser Ala Gly Ala Gly Gln Gly
        355                 360                 365

Gln Ala Ala Trp Xaa Ala Thr Phe Asn Glu Thr Phe Gly Asp Tyr Ser
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Asn His Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
450                 455                 460

Pro Tyr Leu His His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Thr Glu Tyr
        515                 520                 525

Ile Pro Tyr His Phe Arg Pro Asn Tyr His Gly Val Gly Thr Cys Ser
530                 535                 540

Met Met Pro Lys Glu Met Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Ile Ser Asp Ala Ile Leu Glu Asp Tyr Ala Ser Met Gln
        595                 600                 605

<210> SEQ ID NO 15
<211> LENGTH: 579
<212> TYPE: PRT
<213> ORGANISM: Aspergillus niger
<220> FEATURE:
```

<220> FEATURE:
<221> NAME/KEY: MISC_FEATURE
<222> LOCATION: (108)..(108)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (349)..(349)
<223> OTHER INFORMATION: Xaa is Phe, Ala, Leu, Trp or Tyr, provided that
      when Xaa108 is Thr, then Xaa349 is not Phe

<400> SEQUENCE: 15

```
Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Thr
            20                  25                  30

Ala Ala Arg Leu Thr Glu Asn Pro Asp Ile Thr Val Leu Val Ile Glu
        35                  40                  45

Ser Gly Ser Tyr Glu Ser Asp Arg Gly Pro Ile Ile Glu Asp Leu Asn
    50                  55                  60

Ala Tyr Gly Asp Ile Phe Gly Ser Ser Val Asp His Ala Tyr Glu Thr
65                  70                  75                  80

Val Glu Leu Ala Thr Asn Asn Gln Thr Ala Leu Ile Arg Ser Gly Asn
                85                  90                  95

Gly Leu Gly Gly Ser Thr Leu Val Asn Gly Gly Xaa Trp Thr Arg Pro
            100                 105                 110

His Lys Ala Gln Val Asp Ser Trp Glu Thr Val Phe Gly Asn Glu Gly
        115                 120                 125

Trp Asn Trp Asp Ser Val Ala Ala Tyr Ser Leu Gln Ala Glu Arg Ala
    130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
        275                 280                 285

Ser Ala Val Ser Pro Thr Ile Leu Glu Tyr Ser Asp Ile Gly Met Lys
    290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gly Gln Ala Ala Trp Xaa Ala Thr Phe
            340                 345                 350

Asn Glu Thr Phe Gly Asp Tyr Ala Glu Lys Ala His Glu Leu Leu Asn
```

```
                355                 360                 365
Thr Lys Leu Glu Gln Trp Ala Glu Glu Ala Val Ala Arg Gly Gly Phe
370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Val Ala Ser Phe Asp Val Trp Asp Leu Leu Pro Phe Thr Arg Gly
                420                 425                 430

Tyr Val His Ile Leu Asp Lys Asp Pro Tyr Leu Arg His Phe Ala Tyr
                435                 440                 445

Asp Pro Gln Tyr Phe Leu Asn Glu Leu Asp Leu Leu Gly Gln Ala Ala
                450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Ser Ala Trp Val Glu Tyr Ile Pro Tyr Asn Phe Arg Pro Asn
                500                 505                 510

Tyr His Gly Val Gly Thr Cys Ser Met Met Pro Lys Glu Met Gly Gly
                515                 520                 525

Val Val Asp Asn Ala Ala Arg Val Tyr Gly Val Gln Gly Leu Arg Val
530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Ile Leu Ala Asp
                565                 570                 575

Tyr Ala Ser

<210> SEQ ID NO 16
<211> LENGTH: 581
<212> TYPE: PRT
<213> ORGANISM: Aspergillus niger
<220> FEATURE:
<221> NAME/KEY: MISC_FEATURE
<222> LOCATION: (108)..(108)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (349)..(349)
<223> OTHER INFORMATION: Xaa is Phe, Ala, Leu, Trp or Tyr, provided that
      when Xaa108 is Thr, then Xaa349 is not Phe

<400> SEQUENCE: 16

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Thr
                20                  25                  30

Ala Ala Arg Leu Thr Glu Asn Pro Asp Ile Thr Val Leu Val Ile Glu
            35                  40                  45

Ser Gly Ser Tyr Glu Ser Asp Arg Gly Pro Ile Ile Glu Asp Leu Asn
50                  55                  60

Ala Tyr Gly Asp Ile Phe Gly Ser Ser Val Asp His Ala Tyr Glu Thr
65                  70                  75                  80

Val Glu Leu Ala Thr Asn Asn Gln Thr Ala Leu Ile Arg Ser Gly Asn
                85                  90                  95
```

```
Gly Leu Gly Gly Ser Thr Leu Val Asn Gly Gly Xaa Trp Thr Arg Pro
                100                 105                 110

His Lys Ala Gln Val Asp Ser Trp Glu Thr Val Phe Gly Asn Glu Gly
            115                 120                 125

Trp Asn Trp Asp Ser Val Ala Ala Tyr Ser Leu Gln Ala Glu Arg Ala
        130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
210                 215                 220

Asp Ala Ala Arg Glu Trp Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
        275                 280                 285

Ser Ala Val Ser Pro Thr Ile Leu Glu Tyr Ser Gly Ile Gly Met Lys
290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gly Gln Ala Ala Trp Xaa Ala Thr Phe
            340                 345                 350

Asn Glu Thr Phe Gly Asp Tyr Thr Glu Lys Ala His Glu Leu Leu Asn
        355                 360                 365

Thr Lys Leu Glu Gln Trp Ala Glu Glu Ala Val Ala Arg Gly Gly Phe
370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Val Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
        435                 440                 445

Asp Pro Gln Tyr Phe Leu Asn Glu Leu Asp Leu Leu Gly Gln Ala Ala
450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr Asn Phe Arg Pro Asn
            500                 505                 510

Tyr His Gly Val Gly Thr Cys Ser Met Met Pro Lys Glu Met Gly Gly
```

```
            515                 520                 525
Val Val Asp Asn Ala Ala Arg Val Tyr Gly Val Gln Gly Leu Arg Val
        530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
        565                 570                 575

Tyr Ala Ser Met Gln
        580

<210> SEQ ID NO 17
<211> LENGTH: 605
<212> TYPE: PRT
<213> ORGANISM: Aspergillus niger
<220> FEATURE:
<221> NAME/KEY: MISC_FEATURE
<222> LOCATION: (132)..(132)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (373)..(373)
<223> OTHER INFORMATION: Xaa is Phe, Ala, Leu, Trp or Tyr, provided that
      when Xaa132 is Thr, then Xaa373 is not Phe

<400> SEQUENCE: 17

Met Gln Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Asp Val Ser Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asn Ile Ser Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Xaa Trp Thr Arg Pro His Lys Ala Gln Val Asp Ser Trp
    130                 135                 140

Glu Thr Val Phe Gly Asn Glu Gly Trp Asn Trp Asp Asn Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Val Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220

Asp Phe Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255
```

```
Pro Asn Tyr Gln Arg Pro Asn Leu Gln Val Leu Thr Gly Gln Tyr Val
            260                 265                 270

Gly Lys Val Leu Leu Ser Gln Asn Gly Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ala Thr Val Arg Ser Arg Ile Thr Ser Ala Gly Ala Gly Gln Gly
        355                 360                 365

Gln Ala Ala Trp Xaa Ala Thr Phe Asn Glu Thr Phe Gly Asp Tyr Ser
    370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Asn His Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Asp Arg Gly Tyr Val His Ile Leu Asp Lys Asp
    450                 455                 460

Pro Tyr Leu His His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
                485                 490                 495

Ser Asn Ser Gly Ala Met Gln Thr Tyr Phe Ala Gly Glu Ile Leu Pro
            500                 505                 510

Gly Asp Asn Leu Ala Tyr Asp Ala Asp Leu Ser Ala Trp Thr Glu Tyr
        515                 520                 525

Ile Pro Tyr His Phe Arg Pro Asn Tyr His Asp Val Gly Thr Cys Ser
    530                 535                 540

Met Met Pro Lys Glu Met Gly Ser Val Val Asp Asn Ala Ala Arg Val
545                 550                 555                 560

Tyr Gly Val Arg Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Ile Ser Asp Ala Ile Leu Glu Asp Tyr Ala Ser Met Gln
        595                 600                 605

<210> SEQ ID NO 18
<211> LENGTH: 581
<212> TYPE: PRT
<213> ORGANISM: Aspergillus niger
<220> FEATURE:
<221> NAME/KEY: MISC_FEATURE
<222> LOCATION: (108)..(108)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
```

<222> LOCATION: (349)..(349)
<223> OTHER INFORMATION: Xaa is Phe, Ala, Leu, Trp or Tyr, provided that when Xaa108 is Thr, then Xaa349 is not Phe

<400> SEQUENCE: 18

```
Gly Ile Glu Ala Ser Leu Leu Thr Asp Pro Lys Glu Ile Ala Gly Cys
1               5                   10                  15

Thr Val Asp Tyr Ile Ile Ala Gly Gly Leu Thr Gly Leu Thr Thr
            20                  25                  30

Ala Ala Arg Leu Thr Glu Asn Pro Asp Ile Thr Val Leu Val Ile Glu
        35                  40                  45

Ser Gly Ser Tyr Glu Ser Asp Arg Gly Pro Ile Ile Glu Asp Leu Asn
    50                  55                  60

Ala Tyr Gly Asp Ile Phe Gly Ser Ser Val Asp His Ala Tyr Glu Thr
65                  70                  75                  80

Val Glu Leu Ala Thr Asn Asn Gln Thr Ala Leu Ile Arg Ser Gly Asn
                85                  90                  95

Gly Leu Gly Gly Ser Ser Leu Val Asn Gly Gly Xaa Trp Thr Arg Pro
            100                 105                 110

His Lys Ala Gln Val Asp Ser Trp Glu Thr Val Phe Gly Asn Glu Gly
        115                 120                 125

Trp Asn Trp Asp Ser Val Ala Ala Tyr Ser Leu Gln Ala Glu Arg Ala
130                 135                 140

Arg Ala Pro Asn Ala Lys Gln Ile Ala Ala Gly His Tyr Phe Asn Ala
            145                 150                 155                 160

Ser Cys His Gly Ile Asn Gly Thr Val His Ala Gly Pro Arg Asp Thr
            165                 170                 175

Gly Asp Asp Tyr Ser Pro Ile Val Lys Ala Leu Met Ser Ala Val Glu
        180                 185                 190

Asp Arg Gly Val Pro Thr Lys Lys Asp Leu Gly Cys Gly Asp Pro His
    195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
            245                 250                 255

Ala Thr Thr Pro Arg Ala Ile Gly Val Glu Phe Gly Thr His Lys Gly
            260                 265                 270

Asn Thr His Asn Val Tyr Ala Lys His Glu Val Leu Leu Ala Ala Gly
            275                 280                 285

Ser Ala Val Ser Pro Thr Ile Leu Glu Tyr Ser Gly Ile Gly Met Lys
    290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
            325                 330                 335

Thr Ser Ala Gly Ala Gly Gln Gly Gln Ala Ala Trp Xaa Ala Thr Phe
            340                 345                 350

Asn Glu Thr Leu Gly Asp Tyr Ala Glu Lys Ala His Glu Leu Leu Asn
            355                 360                 365

Thr Lys Leu Glu Gln Trp Ala Glu Gly Ala Val Ala Arg Gly Gly Phe
        370                 375                 380

His Asn Thr Thr Ala Leu Leu Ile Gln Tyr Glu Asn Tyr Arg Asp Trp
```

```
                385                 390                 395                 400
Ile Val Lys Asp Asn Val Ala Tyr Ser Glu Leu Phe Leu Asp Thr Ala
                405                 410                 415

Gly Val Ala Ser Phe Gly Val Trp Asp Leu Leu Pro Phe Thr Arg Gly
                420                 425                 430

Tyr Val His Ile Leu Asp Lys Ala Pro Tyr Leu Arg His Phe Ala Tyr
                435                 440                 445

Asp Pro Gln Tyr Phe Leu Asn Glu Leu Asp Leu Leu Gly Gln Ala Ala
            450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                    485                 490                 495

Asp Leu Ser Ala Trp Val Glu Tyr Ile Pro Tyr Asn Phe Arg Pro Asn
                500                 505                 510

Tyr His Gly Val Gly Thr Cys Ser Met Met Pro Lys Glu Met Gly Gly
            515                 520                 525

Val Val Asp Asn Ala Ala Arg Val Tyr Gly Val Gln Gly Gln Arg Val
        530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Ile Leu Ala Asp
                565                 570                 575

Tyr Ala Ser Met Gln
            580

<210> SEQ ID NO 19
<211> LENGTH: 604
<212> TYPE: PRT
<213> ORGANISM: Aspergillus niger
<220> FEATURE:
<221> NAME/KEY: MISC_FEATURE
<222> LOCATION: (131)..(131)
<223> OTHER INFORMATION: Xaa is Ser, Ala, Cys, Ile, Asn, Arg, Asp, Thr,
      Val, Tyr, Glu, His, Met or Gln
<220> FEATURE:
<221> NAME/KEY: MISC_FEATURE
<222> LOCATION: (372)..(372)
<223> OTHER INFORMATION: Xaa is Phe, Ala, Leu, Trp or Tyr, provided that
      when Xaa131 is Thr, then Xaa372 is not Phe

<400> SEQUENCE: 19

Met Lys Thr Ile Leu Ser Ser Ser Leu Val Val Ser Met Ala Ala Ala
1               5                   10                  15

Cys Thr Leu His Arg Ser Ser Gly Ile Glu Ala Ser Leu Leu Thr Asp
                20                  25                  30

Pro Lys Ala Val Ala Gly Arg Thr Val Asp Asp Ile Ala Gly Gly
            35                  40                  45

Gly Leu Thr Gly Leu Thr Thr Ala Ala Arg Leu Thr Glu Asn Pro Asn
        50                  55                  60

Ile Thr Val Leu Val Ile Glu Ser Gly Phe Tyr Glu Ser Asp Arg Gly
65                  70                  75                  80

Pro Leu Val Glu Asp Leu Asn Ala Tyr Gly Glu Ile Phe Gly Ser Glu
                85                  90                  95

Val Asp His Ala Tyr Gln Thr Val Glu Leu Ala Thr Asn Asn Leu Thr
            100                 105                 110

Glu Leu Ile Arg Ser Gly Asn Gly Leu Gly Gly Ser Thr Leu Val Asn
        115                 120                 125
```

```
Gly Gly Xaa Trp Thr Arg Pro His Lys Val Gln Val Asp Ser Trp Glu
130                 135                 140

Thr Val Phe Gly Asn Glu Gly Trp Asn Trp Glu Asn Val Ala Ala Tyr
145                 150                 155                 160

Ser Leu Glu Ala Glu Arg Ala Arg Ala Pro Asn Ala Lys Gln Val Ala
                165                 170                 175

Ala Gly His Tyr Phe Asp Pro Ser Cys His Gly Thr Asn Gly Thr Val
                180                 185                 190

His Val Gly Pro Arg Asp Thr Gly Asp Asp Tyr Thr Pro Ile Ile Asp
                195                 200                 205

Ala Leu Met Thr Thr Val Glu Asn Met Gly Val Pro Thr Lys Lys Asp
210                 215                 220

Leu Gly Cys Gly Asp Pro His Gly Val Ser Met Phe Pro Asn Thr Leu
225                 230                 235                 240

His Glu Asp Gln Val Arg Ser Asp Ala Ala Arg Glu Trp Leu Leu Pro
                245                 250                 255

Asn Tyr Gln Arg Pro Asn Leu Gln Val Leu Thr Gly Gln Leu Val Gly
                260                 265                 270

Lys Val Leu Leu Asp Gln Asn Asn Thr Val Pro Lys Ala Val Gly Val
                275                 280                 285

Glu Phe Gly Thr His Lys Ala Asn Thr Phe Asn Val Tyr Ala Lys His
290                 295                 300

Glu Val Leu Leu Ala Ala Gly Ser Ala Val Ser Pro Gln Ile Leu Glu
305                 310                 315                 320

His Ser Gly Ile Gly Met Lys Ser Ile Leu Asp Thr Val Gly Ile Asp
                325                 330                 335

Thr Val Val Asp Leu Pro Val Gly Leu Asn Leu Gln Asp Gln Thr Ile
                340                 345                 350

Val Leu Val Ser Ser Arg Ile Thr Ser Ala Gly Ala Gly Gln Gly Gln
                355                 360                 365

Val Ala Ile Xaa Ala Thr Phe Asn Glu Thr Phe Gly Asp Tyr Ala Pro
                370                 375                 380

Gln Ala His Ala Leu Leu Asp Ala Lys Leu Glu Gln Trp Ala Glu Glu
385                 390                 395                 400

Gly Val Ala Arg Gly Gly Phe His Asn Ala Thr Ala Leu Arg Ile Gln
                405                 410                 415

Tyr Glu Asn Tyr Arg Asp Trp Leu Val Asn His Asn Val Ala Tyr Ser
                420                 425                 430

Glu Leu Phe Leu Asp Thr Ala Gly Ala Val Ser Phe Thr Ile Trp Asp
                435                 440                 445

Leu Ile Pro Phe Thr Arg Gly Tyr Val His Ile Thr Asp Ala Asp Pro
450                 455                 460

Tyr Leu Arg Leu Val Ser Tyr Asp Pro Gln Tyr Phe Leu Asn Glu Leu
465                 470                 475                 480

Asp Leu Tyr Gly Gln Ala Ala Ser Gln Leu Ala Arg Asn Leu Ser
                485                 490                 495

Asn Thr Asp Ala Met Gln Thr Tyr Phe Ala Gly Glu Thr Thr Pro Gly
                500                 505                 510

Asp Asn Pro Ala Tyr Asp Ala Ser Leu Ser Asp Trp Ala Glu Tyr Ile
                515                 520                 525

Lys Tyr Asn Phe Arg Pro Asn Tyr His Gly Val Gly Thr Cys Ser Met
530                 535                 540
```

Met Lys Lys Glu Leu Gly Gly Val Val Asp Ser Ser Ala Arg Val Tyr
545                 550                 555                 560

Gly Val Asp Ser Leu Arg Val Ile Asp Gly Ser Ile Pro Pro Thr Gln
                565                 570                 575

Val Ser Ser His Val Met Thr Val Phe Tyr Ala Met Ala Leu Lys Ile
            580                 585                 590

Ser Ala Ala Ile Leu Ala Asp Tyr Ala Ser Ser Gln
        595                 600

<210> SEQ ID NO 20
<211> LENGTH: 619
<212> TYPE: PRT
<213> ORGANISM: Sclerotinia sclerotiorum
<220> FEATURE:
<221> NAME/KEY: MISC_FEATURE
<222> LOCATION: (130)..(130)
<223> OTHER INFORMATION: Xa

```
            260                 265                 270
Gly Lys Val Leu Leu Asn Ser Gln Pro Glu Ala Ile Gln Ala His Gly
            275                 280                 285

Val Gln Phe Gly Thr Asn Arg His Ser Asn Phe Glu Val Tyr Ala Arg
        290                 295                 300

His Glu Val Leu Leu Ala Ala Gly Ala Leu Ser Ser Pro Leu Ile Leu
305                 310                 315                 320

Glu Tyr Ser Gly Ile Gly Ile Lys Lys Val Leu Glu Asn Ala Asn Val
                325                 330                 335

Ser Gln Val Leu Glu Leu Pro Val Gly Ile Asn Val Gln Asp Gln Thr
            340                 345                 350

Thr Thr Thr Val Arg Ser Glu Ile Asn Asp Leu Gly Tyr Gly Gln Gly
        355                 360                 365

Gln Ala Ile Tyr Xaa Ala Thr Phe Asn Glu Thr Phe Gly Lys Tyr Ser
    370                 375                 380

Ser Leu Ala His Asn Leu Leu Asn Lys Asn Leu Lys Arg Trp Ala Arg
385                 390                 395                 400

Glu Thr Val Asp Asn Gly Gly Phe Asn Asn Ile Thr Ala Leu Ile Ile
                405                 410                 415

Gln Tyr Glu Asn Tyr Arg Asp Trp Leu Thr Lys Asp Asn Ile Ala Tyr
            420                 425                 430

Ser Glu Leu Phe Met Asp Thr Glu Gly Ala Ile Asn Phe Asp Leu Trp
        435                 440                 445

Thr Leu Ile Pro Phe Thr Arg Gly Phe Val His Ile Leu His Arg Asp
    450                 455                 460

Pro Tyr Leu Arg His Val Met Thr Asn Pro Arg Tyr Phe Gly Asn Glu
465                 470                 475                 480

Leu Asp Ile Leu Gly Gln Ala Ala Ala Ser Lys Leu Ala Arg Asp Leu
                485                 490                 495

Ser Asp Ala Gly Ser Met Ala Arg Phe Tyr Glu Lys Glu Val Ile Pro
            500                 505                 510

Gly Ala Thr Lys Leu Lys Pro Asp Ala Asn Leu Asp Glu Trp Ile Ser
        515                 520                 525

Tyr Val Lys Gln Asn Phe Arg Pro Asn Tyr His Asn Val Gly Ser Cys
    530                 535                 540

Ser Met Met Ala Arg Glu Leu Gly Gly Val Val Asn Pro Gln Gly Lys
545                 550                 555                 560

Val Tyr Asp Val His Gly Leu Arg Val Ile Asp Ala Ser Val Val Pro
                565                 570                 575

Thr Gln Val Ser Ala His Ile Met Thr Val Leu Tyr Gly Met Ala Val
            580                 585                 590

Lys Ile Ser Ala Asp Ile Met Val Asp Tyr His Val Lys Met Glu Lys
        595                 600                 605

Ser Met Leu Glu Thr Ala Lys Leu Glu Leu Lys
    610                 615

<210> SEQ ID NO 21
<211> LENGTH: 655
<212> TYPE: PRT
<213> ORGANISM: Aspergillus niger
<220> FEATURE:
<221> NAME/KEY: MISC_FEATURE
<222> LOCATION: (163)..(163)
<223> OTHER INFORMATION: Xaa is Ser, Ala, Cys, Ile, Asn, Arg, Asp, Thr,
      Val, Tyr, Glu, His, Met or Gln
<220> FEATURE:
```

```
<221> NAME/KEY: MISC_FEATURE
<222> LOCATION: (422)..(422)
<223> OTHER INFORMATION: Xaa is Phe, Ala, Leu, Trp or Tyr, provided that
      when Xaa163 is Thr, then Xaa422 is not Phe
<220> FEATURE:
<221> NAME/KEY: MISC_FEATURE
<222> LOCATION: (441)..(441)
<223> OTHER INFORMATION: Xaa is any amino acid

<400> SEQUENCE: 21
```

| | | | | | | | | | | | | | | |
|---|---|---|---|---|---|---|---|---|---|---|---|---|---|---|
| Met | Lys | Phe | Pro | Ile | Leu | Ala | Ser | Ala | Leu | Leu | Leu | Ser | Gly | Val | Leu |
| 1 | | | | 5 | | | | | 10 | | | | | 15 |

| Ala | Glu | His | Phe | Gln | Val | Pro | Leu | Gln | His | Thr | Ile | Ser | Pro | Cys | Ser |
|---|---|---|---|---|---|---|---|---|---|---|---|---|---|---|---|
| | | | 20 | | | | | 25 | | | | | 30 | | |

| Thr | Lys | Pro | His | Thr | Ser | His | Asp | Asp | Leu | Asn | His | Asn | Ile | Asn | Thr |
|---|---|---|---|---|---|---|---|---|---|---|---|---|---|---|---|
| | | 35 | | | | | 40 | | | | | 45 | | | |

| Ile | Pro | His | Gly | Ile | Thr | Asp | Asp | Pro | Arg | Ser | Ile | Asp | Asn | Gln | Thr |
|---|---|---|---|---|---|---|---|---|---|---|---|---|---|---|---|
| | 50 | | | | | 55 | | | | | 60 | | | | |

| Phe | Asp | Tyr | Ile | Ile | Ala | Gly | Gly | Leu | Thr | Gly | Leu | Thr | Leu | Ala |
|---|---|---|---|---|---|---|---|---|---|---|---|---|---|---|
| 65 | | | | | 70 | | | | | 75 | | | | 80 |

| Ala | Lys | Leu | Val | Glu | Gln | Lys | Lys | Tyr | Thr | Val | Leu | Val | Ile | Glu | Ser |
|---|---|---|---|---|---|---|---|---|---|---|---|---|---|---|---|
| | | | | 85 | | | | | 90 | | | | | 95 | |

| Gly | Phe | Tyr | Ala | Trp | Glu | Tyr | Gly | Pro | Lys | Ile | Asp | Asp | Leu | Asn | Thr |
|---|---|---|---|---|---|---|---|---|---|---|---|---|---|---|---|
| | | | 100 | | | | | 105 | | | | | 110 | | |

| Tyr | Gly | Gln | Val | Phe | Gly | Ser | Ser | Val | Asp | His | Ala | Tyr | Glu | Thr | Ser |
|---|---|---|---|---|---|---|---|---|---|---|---|---|---|---|---|
| | | 115 | | | | | 120 | | | | | 125 | | | |

| Pro | Gln | Leu | Val | Gly | Asn | Asp | Gly | Glu | Thr | Gly | Leu | Asp | Lys | Asp | Ile |
|---|---|---|---|---|---|---|---|---|---|---|---|---|---|---|---|
| | 130 | | | | | 135 | | | | | 140 | | | | |

| Arg | Ile | Val | Arg | Ser | Gly | Asn | Gly | Leu | Gly | Gly | Ser | Thr | Leu | Ile | Asn |
|---|---|---|---|---|---|---|---|---|---|---|---|---|---|---|---|
| 145 | | | | | 150 | | | | | 155 | | | | | 160 |

| Gly | Gly | Xaa | Trp | Thr | Arg | Pro | His | Lys | Ser | Gln | Leu | Asp | Ser | Trp | Glu |
|---|---|---|---|---|---|---|---|---|---|---|---|---|---|---|---|
| | | | | 165 | | | | | 170 | | | | | 175 | |

| Glu | Val | Phe | Gly | Asn | Thr | Gly | Trp | Asn | Trp | Asp | Ala | Leu | Lys | Gly | Lys |
|---|---|---|---|---|---|---|---|---|---|---|---|---|---|---|---|
| | | | 180 | | | | | 185 | | | | | 190 | | |

| Met | Asp | Glu | Ile | Glu | Val | Pro | Arg | Asp | Pro | Thr | Ser | Asp | Asp | Ile | Thr |
|---|---|---|---|---|---|---|---|---|---|---|---|---|---|---|---|
| | | 195 | | | | | 200 | | | | | 205 | | | |

| Lys | Gly | Ser | Phe | His | Lys | Phe | Asp | Ala | Glu | Cys | His | Asn | Lys | Glu | Pro |
|---|---|---|---|---|---|---|---|---|---|---|---|---|---|---|---|
| | 210 | | | | | 215 | | | | | 220 | | | | |

| Glu | Lys | Gly | Lys | Val | Lys | Val | Gly | Ala | Arg | Asp | Arg | Lys | Tyr | Gly | Trp |
|---|---|---|---|---|---|---|---|---|---|---|---|---|---|---|---|
| 225 | | | | | 230 | | | | | 235 | | | | | 240 |

| Ser | Pro | Leu | Ile | Arg | Ala | Leu | Met | His | Thr | Val | Asn | Ser | Thr | Tyr | Glu |
|---|---|---|---|---|---|---|---|---|---|---|---|---|---|---|---|
| | | | | 245 | | | | | 250 | | | | | 255 | |

| Glu | Val | Val | Asn | Gln | Lys | Asp | Leu | Cys | Cys | Gly | Asp | Pro | Thr | Gly | Val |
|---|---|---|---|---|---|---|---|---|---|---|---|---|---|---|---|
| | | | 260 | | | | | 265 | | | | | 270 | | |

| Ser | Met | Phe | Leu | Asn | Thr | Leu | Thr | Asn | Glu | Gln | Ile | Arg | Thr | Asp | Ala |
|---|---|---|---|---|---|---|---|---|---|---|---|---|---|---|---|
| | | 275 | | | | | 280 | | | | | 285 | | | |

| Ala | Arg | Ser | Trp | Leu | Lys | Pro | Ile | Leu | Asp | Asp | Glu | Leu | Lys | Gln |
|---|---|---|---|---|---|---|---|---|---|---|---|---|---|---|
| | 290 | | | | | 295 | | | | | 300 | | | |

| Tyr | Ile | Thr | Val | Leu | Thr | Gly | Glu | Leu | Val | Gly | Lys | Val | His | Leu | Asn |
|---|---|---|---|---|---|---|---|---|---|---|---|---|---|---|---|
| 305 | | | | | 310 | | | | | 315 | | | | | 320 |

| Glu | Ala | Asn | Pro | Ser | Glu | Thr | Gly | Thr | Glu | Phe | Lys | Ala | Lys | Gly | Val |
|---|---|---|---|---|---|---|---|---|---|---|---|---|---|---|---|
| | | | | 325 | | | | | 330 | | | | | 335 | |

| Glu | Phe | Gly | Val | His | Lys | Lys | Gln | Glu | Trp | Lys | Trp | Asp | Ala | Trp | Ala |
|---|---|---|---|---|---|---|---|---|---|---|---|---|---|---|---|
| | | | 340 | | | | | 345 | | | | | 350 | | |

| Arg | Lys | Glu | Val | Leu | Leu | Ala | Ala | Gly | Ser | Thr | Ile | Ser | Pro | Leu | Ile |
|---|---|---|---|---|---|---|---|---|---|---|---|---|---|---|---|
| | | 355 | | | | | 360 | | | | | 365 | | | |

```
Leu Gln Trp Ser Gly Ile Gly Pro Lys Val Trp Leu Asp Ala Ala Gly
        370                 375                 380

Ile Glu His Lys Leu Glu Leu Pro Val Gly Tyr Asn Leu Gln Asp Gln
385                 390                 395                 400

Thr Thr Thr Ser Val Val Thr Lys Pro Lys Pro Glu Ala Asn Gly Gln
                405                 410                 415

Gly Gln Ala Ala Tyr Xaa Ala Thr Phe Ala Glu Ile Phe Gly Lys Asp
                420                 425                 430

Ala Ser Asp Met Glu Lys Leu Leu Xaa Asp Asp Thr Glu Leu Asp Lys
            435                 440                 445

Trp Ala Glu His Thr Val Asn Gly His Gly Phe Pro Asp Lys Ala Asn
        450                 455                 460

Leu Leu Lys Gln Tyr Lys Asn Tyr Arg Asp Trp Leu Leu Thr Asp Lys
465                 470                 475                 480

Val Ser Tyr Ala Glu Leu Phe Leu Asp Thr Asp Asn Ser Thr His Phe
                485                 490                 495

Asp Leu Trp Asn Leu Ile Pro Phe Thr Arg Gly Tyr Val Lys Ile Leu
            500                 505                 510

Asp Asn Asp Pro Tyr Leu Arg Ser Phe Glu Tyr Asn Pro Arg Tyr Phe
        515                 520                 525

Glu Asn Ile Leu Asp Leu Asn Gly Gln Ala Ala Thr Arg Leu Ala
530                 535                 540

Arg Gln Leu Thr Asn Thr Tyr Asp Met Lys Gln Tyr Val Asp Lys Glu
545                 550                 555                 560

Gln Val Pro Gly Arg Tyr Val Pro Glu Asn Ala Asn Leu Thr Glu Trp
                565                 570                 575

Ala Asp Tyr Val Lys Gln Asn Tyr Arg Ala Asn Tyr His Gly Val Gly
            580                 585                 590

Thr Cys Ser Met Met Lys Lys Glu Leu Gly Gly Val Val Asp Pro Glu
        595                 600                 605

Ala Lys Val Tyr Gly Val Glu Gly Leu Arg Val Val Asp Gly Ser Ile
610                 615                 620

Pro Pro Thr Gln Val Ser Ser His Val Met Thr Val Phe Tyr Ala Met
625                 630                 635                 640

Ala Val Lys Ile Ala Glu Ser Val Ile Lys Asp Ala Gly Asn Ala
                645                 650                 655

<210> SEQ ID NO 22
<211> LENGTH: 30
<212> TYPE: DNA
<213> ORGANISM: Artificial Sequence
<220> FEATURE:
<223> OTHER INFORMATION: primer for point mutation

<400> SEQUENCE: 22
cttgataaac ggtgacgcgt ggactcgccc                              30

<210> SEQ ID NO 23
<211> LENGTH: 30
<212> TYPE: DNA
<213> ORGANISM: Artificial Sequence
<220> FEATURE:
<223> OTHER INFORMATION: primer for point mutation

<400> SEQUENCE: 23
gggcgagtcc acgcgtcacc gtttatcaag                              30
```

<210> SEQ ID NO 24
<211> LENGTH: 30
<212> TYPE: DNA
<213> ORGANISM: Artificial Sequence
<220> FEATURE:
<223> OTHER INFORMATION: primer for point mutation

<400> SEQUENCE: 24
caggccgtct tcgcggccaa tttcactgag         30

<210> SEQ ID NO 25
<211> LENGTH: 30
<212> TYPE: DNA
<213> ORGANISM: Artificial Sequence
<220> FEATURE:
<223> OTHER INFORMATION: primer for point mutation

<400> SEQUENCE: 25
ctcagtgaaa ttggccgcga agacggcctg         30

<210> SEQ ID NO 26
<211> LENGTH: 30
<212> TYPE: DNA
<213> ORGANISM: Artificial Sequence
<220> FEATURE:
<223> OTHER INFORMATION: primer for point mutation

<400> SEQUENCE: 26
gtcaggccgt cttcctggcc aatttcactg         30

<210> SEQ ID NO 27
<211> LENGTH: 32
<212> TYPE: DNA
<213> ORGANISM: Artificial Sequence
<220> FEATURE:
<223> OTHER INFORMATION: primer for point mutation

<400> SEQUENCE: 27
ctcagtgaaa ttggccagga agacggcctg ac         32

<210> SEQ ID NO 28
<211> LENGTH: 30
<212> TYPE: DNA
<213> ORGANISM: Artificial Sequence
<220> FEATURE:
<223> OTHER INFORMATION: primer for point mutation

<400> SEQUENCE: 28
caggccgtct tcccggccaa tttcactgag         30

<210> SEQ ID NO 29
<211> LENGTH: 30
<212> TYPE: DNA
<213> ORGANISM: Artificial Sequence
<220> FEATURE:
<223> OTHER INFORMATION: primer for point mutation

<400> SEQUENCE: 29
ctcagtgaaa ttggccggga agacggcctg         30

<210> SEQ ID NO 30
<211> LENGTH: 30
<212> TYPE: DNA
<213> ORGANISM: Artificial Sequence
<220> FEATURE:
<223> OTHER INFORMATION: primer for point mutation

```
<400> SEQUENCE: 30
caggccgtct tctgggccaa tttcactgag                                    30

<210> SEQ ID NO 31
<211> LENGTH: 30
<212> TYPE: DNA
<213> ORGANISM: Artificial Sequence
<220> FEATURE:
<223> OTHER INFORMATION: primer for point mutation

<400> SEQUENCE: 31
ctcagtgaaa ttggcccaga agacggcctg                                    30

<210> SEQ ID NO 32
<211> LENGTH: 26
<212> TYPE: DNA
<213> ORGANISM: Artificial Sequence
<220> FEATURE:
<223> OTHER INFORMATION: primer for point mutation

<400> SEQUENCE: 32
caggccgtct tctacgccaa tttcac                                        26

<210> SEQ ID NO 33
<211> LENGTH: 26
<212> TYPE: DNA
<213> ORGANISM: Artificial Sequence
<220> FEATURE:
<223> OTHER INFORMATION: primer for point mutation

<400> SEQUENCE: 33
gtgaaattgg cgtagaagac ggcctg                                        26
```